US005717075A

United States Patent [19]
Boyd et al.

[11] Patent Number: 5,717,075
[45] Date of Patent: Feb. 10, 1998

[54] IMMOBILIZATION OF POLYPEPTIDES ON A POLYVINYLIDENE DIFLUORIDE MEMBRANE CONTAINING ENOL ESTER AND SULFONATE GROUPS

[75] Inventors: Victoria Lee Boyd, San Carlos; Pau-Miau Yuan, San Jose, both of Calif.

[73] Assignee: The Perkin-Elmer Corporation, Foster City, Calif.

[21] Appl. No.: 623,431

[22] Filed: Mar. 28, 1996

Related U.S. Application Data

[60] Division of Ser. No. 129,607, Sep. 29, 1993, Pat. No. 5,602,207, which is a continuation-in-part of Ser. No. 3,197, Jan. 11, 1993, abandoned.

[51] Int. Cl.⁶ .................... C07K 17/06; C07K 17/08; C12N 11/08; C12N 11/06
[52] U.S. Cl. .................... 530/402; 435/176; 435/180; 435/181; 436/89; 525/326.2; 530/334; 530/811; 530/815; 530/816
[58] Field of Search ................... 435/174, 176, 435/177, 180, 181; 436/89, 524, 531, 532; 530/334, 402, 811, 815, 816; 525/326.2

[56] References Cited

U.S. PATENT DOCUMENTS

| | | | |
|---|---|---|---|
| 4,289,853 | 9/1981 | Bailey et al. | 435/177 |
| 5,041,388 | 8/1991 | Boyd et al. | 436/89 |
| 5,049,507 | 9/1991 | Hawke et al. | 436/89 |
| 5,051,368 | 9/1991 | Boyd et al. | 436/89 |
| 5,185,266 | 2/1993 | Boyd et al. | 436/89 |
| 5,304,497 | 4/1994 | Boyd et al. | 436/89 |
| 5,306,781 | 4/1994 | Bailey | 525/333.9 |

OTHER PUBLICATIONS

Zaborsky, O., Immobilized Enzymes, CRC Press, Cleveland, Ohio, 1973, p. 25.
Aebersold, R., et al., "Covalent Attachment of Peptides for High Sensitivity Solid–Phase Sequence Analysis," *Analytical Chem.* 187:56–65 (1990).
Bailey, J.M., et al., "Automated Carboxy–Terminal Sequence Analysis of Peptides," *Protein Sci.* 1:68–80 (1992a).
Bailey, J.M., et al., "Automated Carboxy–Terminal Sequence Analysis of Peptides and Proteins Using Diphenyl Phosphoroisothio–cyanatidate," *Protein Sci.* 1:1622–1633 (1992b).
Bailey, J.M., et al., "Automated C–Terminal Sequencing of Peptides," in *Techniques In Protein Chemistry III* (Academic Press, San Diego, CA) pp. 11–21 (1992c).
Boyd, V.L., et al., "Synthesis of the 2–Thiohydantoins of Amino Acids Using Woodward's Reagent K," *Tetrahedron Lett.* 31:(27):3849–3852 (1990).
Coull, J.M., et al., "Functionalized Membrane Supports for Covalent Protein Microsequence Analysis," *Analytical Chem.* 194:110–120 (1991).
Inglis, A.S., "Chemical Procedures for C–Terminal Sequencing of Peptides and Proteins," *Analytical Chem.* 195:183–196 (1991).
Pappin, D.J.C., et al., "Solid–Phase Sequence Analysis of Proteins Electroblotted or Spotted onto Polyvinylidene Difluoride Membranes," *Analytical Biochem.* 187:10–19 (1990).
Shenoy, N.R., et al., "Carboxylic Acid–Modified polyethylene: A Novel Support for the Covalent Immobilization of Polypeptides for C–Terminal Sequencing," *Protein Sci.* 1:58–67 (1992).
Woodward, R.B., and Olofson, R.A., "The Reaction of Isoxazolium Salts with Nucleophiles," *Tetrahedron Supp.* 7:415–440 (1966).

*Primary Examiner*—David M. Naff
*Attorney, Agent, or Firm*—Vincent M. Powers; Karen Guerrero

[57] ABSTRACT

A solid support having surface-attached carboxylic acid groups is reacted with an isoxazolium salt to form an activated support having enol ester and sulfonate groups. After washing to remove residual isoxazolium salt and base, the activated support is dried. A polypeptide is covalently or non-covalently bound to the support. The resultant immobilized polypeptide can be conveniently sequenced by N- and C-terminal sequencing methods. The support can be a polyvinylidene difluoride membrane or a glass fiber membrane having surface attached carboxylic acid groups, and the enol and sulfonate groups are provided by reacting the support with 2-ethyl-5'-phenylisoxazolium sulfonate. The dry support can be stored for at least about 3 months to achieve a peptide immobilization yield that is substantially the same as the yield obtained in the absence of drying.

4 Claims, 22 Drawing Sheets

SEQ ID NO:1
Ala Lys Gly Lys Gly Lys Leu Tyr Phe Gly Leu Tyr
Gln Phe Gly

SEQ ID NO:2
Gly Ala Pro Lys Gly Lys Gly Lys Tyr Phe Leu Tyr

SEQ ID NO:3
Lys Gly Lys Gly Lys Gly Leu Gln Asn Leu Ala

SEQ ID NO:4
Leu Glu His Phe Arg Lys Gly Ile Gln Val Asn Tyr

IMMOBILIZATION OF POLYPEPTIDES ON A POLYVINYLIDENE DIFLUORIDE MEMBRANE CONTAINING ENOL ESTER AND SULFONATE GROUPS

This application is a division of application Ser. No. 08/129,607, filed Sep. 29, 1993, now U.S. Pat. No. 5,602,207, which is a continuation-in-part of application Ser. No. 08/003,197, filed Jan. 11, 1993, now abandoned.

FIELD OF THE INVENTION

The present invention relates to a solid support and method for immobilizing polypeptides, and in particular, to a solid support and method for use in polypeptide sequencing.

REFERENCES

Aebersold, R. H., et al., (1988) *Biochem.* 27(18):6860–6867.
Allen, G. (1981) *Sequencing of Proteins and Peptides*, Elsevier Science Publishers, Amsterdam, The Netherlands.
Bridgen, J. (1975) *FEBS Lett.* 35:97–102.
Coull, J. M., et al., (1991) *Anal. Biochem.* 194:110–120.
Dias, A. J., et al., (1987) *Macromolecules* 20:2074–2075.
Findlay, J. B. C. and Geisow, M. J., Eds (1989) *Protein Sequencing: A Practical Approach* IRL Press, Oxford, England.
Laursen, R. A. and Machleidt, W. (1980) In: *Methods of Biochemical Analysis* 26:201–284.
Lee, K.-W., et al., (1987) *Macromolecules* 20:1437–1439.
Matsudaira, P. (1987) *J. Biol. Chem.* 262:10035.
Woodward, R. B. and Olofson, R. A. *J. Am. Chem. Soc.* 83:1007 (1961) 83:1007–1009; Tetrahedron Suppl. No. 7 (1966) pp. 415–440.

BACKGROUND OF THE INVENTION

In solid-phase peptide sequencing, a polypeptide is immobilized on a solid support, and a series of chemical reactions are carried out sequentially to release and identify amino acid residues from the C- or N-terminal end of the polypeptide (Coull).

The most widely used method for N-terminal sequencing involves reacting the N-terminal amino group of the polypeptide with phenyl isothiocyanate (PITC), in a process known as Edman degradation (Edman). The reaction of PITC with the terminal amino group adds a phenylthiourea group, which cyclizes and cleaves, forming a free anilinothiozolanone (ATZ) of the N-terminal amino acid, and a shortened peptide. The ATZ-derivative of the N-terminal amino acid is separated, converted to the corresponding phenylthiohydantoin (PTH), and identified by high performance liquid chromatography (HPLC). Sequencing is then carried out by successively converting the next-in N-terminal residue to a free amino acid PTH, and identifying each successively released amino acid. The method is generally reliable for sequences up to about 20–40 amino acid residues and is readily performed with automated instrumentation.

At the present time, most C-terminal sequencing involve the formation of a C-terminal thiohydantoin (TH) or thiohydantoin-like derivative. In one approach, the C-terminal carboxyl group of a polypeptide is activated using acetic anhydride in the presence of an isothiocyanate (ITC) salt or acid to form a C-terminal thiohydantoin via a C-terminal ITC intermediate (Stark). The C-terminal thiohydantoin can be cleaved from the polypeptide, producing a shortened peptide and the thiohydantoin derivative of the C-terminal amino acid residue. This derivative can be separated and identified, e.g., by HPLC.

Two general approaches have been used for immobilizing polypeptides on a solid support for sequence analysis. In one approach, the polypeptide is immobilized by covalent attachment to the support via reactive groups on the support. For N-terminal sequencing, the C-terminal carboxylic acid group can be reacted with an activating reagent, such as carbonyldiimidazole or carbodiimide, for subsequent coupling to support-bound amino groups (Laursen). Covalent attachment via side chain groups of internal residues is also possible (Findlay and Geisow, 1989).

For N-terminal sequencing, DITC-activated glass is commonly used, where support-bound isothiocyanate groups react with polypeptide amino groups (i.e., lysyl ε-amino groups) to form stable thiourea linkages with the polypeptide (Bridgen). The α-amino group of the polypeptide can also react with the support, but such linkages (with α-amino groups) can be cleaved using trifluoroacetic acid (TFA) (Allen, 1981).

Covalent attachment using activated supports offers the advantage of essentially permanent immobilization of the polypeptide on the support, thereby minimizing sample wash-out. However, activated supports tend to be susceptible to inactivation by water. Thus, polypeptide samples must be dissolved in special, non-aqueous solvents (e.g., acetonitrile) prior to immobilization on the support. In addition, the efficiencies of immobilization are often inconsistent because the activating groups deteriorate over time.

In a second approach, the polypeptide is immobilized noncovalently. In gas-liquid solid-phase sequencing, for example, the sample is typically entrained in a membrane-type support by ionic and hydrogen-bonding interactions with the polypeptide. Glass fiber supports have proven useful for this application, although other support-types can be used. For example, proteins resolved by SDS-polyacrylamide gel electrophoresis can be electroblotted directly onto polyvinylidene difluoride (PVDF) membranes, and the part of the membrane containing the protein of interest can be loaded directly into an automated sequencer (Matsudaira, 1987).

Although supports for non-covalent binding avoid the problems of activating group stability, such supports usually fail to retain small polypeptides. The efficiency and longevity of immobilization can often be improved by adding to the support a polycationic carrier, such as "POLYBREEN", which forms a matrix on the surface of the support to enhance retention of the polypeptide. One drawback, however, is that such matrices usually require precycling, i.e., treatment of the matrix-coated support with several sequencing cycles prior to sample loading, to remove contaminants from the matrix which would otherwise interfere with amino acid identification during sequence analysis. Thus, use of such matrices can slow the sequencing protocol.

Ideally, an activated support for covalent immobilization of polypeptides should react readily with polypeptides. The support should be compatible with aqueous polypeptide samples, and should be storable for extended periods of time without losing binding efficiency.

SUMMARY OF THE INVENTION

In one aspect, the invention is directed to a method for immobilizing a polypeptide on a solid support. In the method, a solid support having surface-attached carboxylic acid groups is reacted with an isoxazolium salt to form an activated support. After the activated support has been washed to remove residual isoxazolium salt and base, the support is air-dried. The dried support is then contacted with a polypeptide under conditions effective to bind the polypeptide covalently to the support.

In one embodiment, the solid support includes surface-attached sulfonate groups, for binding noncovalently with cationic charged groups in the polypeptide.

The invention also includes a solid support for use in the method above, having surface-attached enol ester groups which are reactive with one or more amino groups in the polypeptide. The support is compatible with aqueous polypeptide samples, and can be stored in dry form (i.e., after air-drying) for extended periods, e.g., several months, without a reduction in immobilization efficiency. In one preferred embodiment, the support comprises a polyvinylidene difluoride membrane. In addition, the support may include surface-attached sulfonate groups, for binding non-covalently with cationic charged groups in the polypeptide as noted above.

In another aspect, the invention includes a method for immobilizing a polypeptide, wherein a solid support of the type just described is contacted with a polypeptide under conditions effective to bind the polypeptide to the membrane.

In another aspect, the invention includes a method for identifying sequence positions of N-terminal and C-terminal residues in a polypeptide. In the method, a polypeptide having a C-terminal carboxylic acid group is contacted with a polyvinylidene difluoride membrane having surface-attached enol ester groups under conditions effective to immobilize the polypeptide covalently or non-covalently to the membrane. After polypeptide immobilization, the membrane is subjected to one or more cycles of Edman degradation, to determine the sequence of one or more N-terminal residues in the bound polypeptide. The same membrane is then subjected to one or more cycles of C-terminal sequencing, to determine the sequence of one or more C-terminal residues in the polypeptide.

These and other objects and features of the present invention will become more fully apparent when the following detailed description of the invention is read in conjunction with the accompanying drawings.

DETAILED DESCRIPTION OF THE INVENTION

I. Definitions

Figure 1:
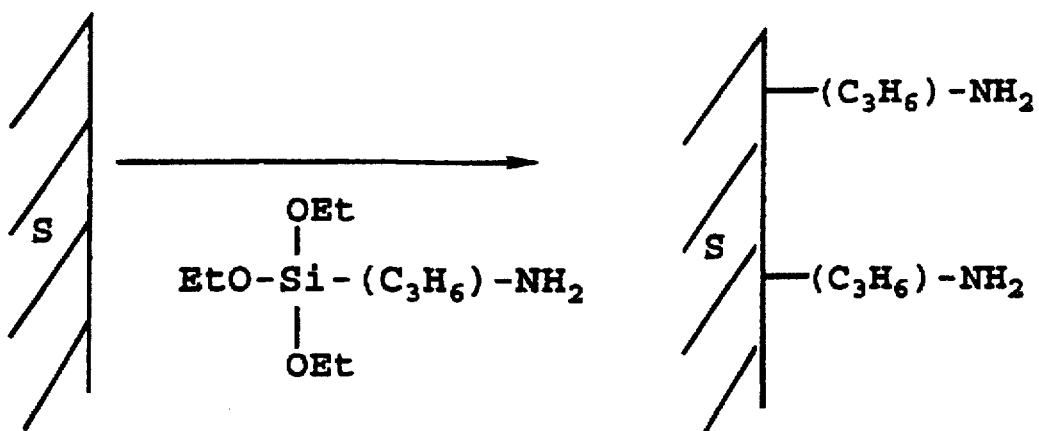
FIG. 1 illustrates modification of a glass solid support (S) by reaction with aminopropyl-(triethoxysilane)

Unless stated otherwise, the terms below have the following meanings:

"Activated support" or "activated solid support" refers to a solid support having surface-attached chemical groups capable of reacting with a polypeptide to form a covalent bond between the polypeptide and the support.

"Polypeptide" refers to multiple amino acid residues linked by peptide (amide) linkages. As used herein, "polypeptide" includes short peptides (i.e., peptides 2 to about 20 amino acid residues) as well as much longer polypeptides, that is, proteins, such as apomyoglobin or lysozyme.

"Peptide" refers to a polypeptide containing from 2 to about 50 amino acid residues.

Abbreviations for amino acid residues are the standard 3-letter and/or 1-letter codes used in the art.

II. General Features of the Invention

The present invention includes a method for immobilizing a polypeptide on a solid support. In one embodiment, the method includes derivatizing carboxylic acid groups on a suitable support with an N-substituted isoxazolium compound, such as N-ethyl-5'-phenylisoxazoliumsulfonate (Woodward's Reagent K; WRK), typically in an organic solvent in the presence of base. This derivatization reaction converts the support-bound carboxylic acid groups to enol ester groups, which are "activated" for attack by nucleophiles. After the activation reaction, residual isoxazolium salt and base are removed and the support is air-dried for long-term storage. According to an important aspect of the invention, the inventors have found that the dried, activated support can be stored for an extended period of time (e.g., several months), without diminishing the immobilization effeciency of the support. In a particularly advantageous embodiment of the invention, the solid support comprises a polyvinylidene difluoride (PVDF) membrane.

Polypeptide immobilization can be effected by contacting the polypeptide with the dried support under conditions effective to promote reaction of a polypeptide amino group with a support-bound enol ester group, to attach the polypeptide covalently to the support. Such covalent attachment may be achieved in the presence of an organic solvent (e.g., acetonitrile, methanol, or N-methyl pyrrolidone), or alternatively, in an aqueous solution at a pH of between about 1 and about 8. In general, reaction times may range from about 3 to 24 hours, typically 3 to 6 hours. Much shorter reaction times may also be effective for efficient immobilization, e.g., on the order of minutes, particularly where the support comprises a PVDF membrane. Prior to sequence analysis, non-bound polypeptide may be removed by washing the membrane with solvent.

Immobilization of a polypeptide on the support leaves the C-terminal end of a peptide free for C-terminal sequencing by, for example, the method disclosed in Boyd and Zon in U.S. Pat. No. 5,185,266, which is incorporated herein by reference in its entirety.

III. Activated Solid Support

This section describes appropriate solid supports, activating reagents and reactions for generating activated (reactive) solid supports of the invention.

A. Carboxylated Solid Support

A variety of solid support materials and configurations can be used for peptide immobilization in accordance with the present invention. Suitable configurations include beads, resins, and membranes, for example. Suitable support materials include glass (e.g., CPG beads); and polymer materials such as nylon, polystyrene, modified polyethylene, "TEFLON", and polystyrene resin embedded in Teflon.

A support for forming the activated support of the invention includes support-bound carboxylic acid groups, or else chemical groups that can be converted to carboxylic acid groups by known reaction schemes. Exemplary supports for this purpose include Bio-Rex 70 (Bio-Rad, Richmond, Calif.), a cation exchange resin which has a carboxylic acid group density of 10 meq/g; aminopropyl controlled pore glass (CPG) beads and aminomethyl polystyrene beads (Applied Biosystems, Inc. Foster City, Calif.), which can be converted to carboxyl groups prior to activation; and Amberlite IRP 64 (Rohm and Haas), another carboxylate-containing cation exchange resin. A preferred solid support is a polyvinylidene difluoride membrane derivatized with carboxylic acid groups (PVDF-COOH). One such membrane is commercially available from Pall Corporation (Long Island, N.Y.). Alternatively, carboxylated PVDF membranes can be prepared by methods known in the art.

FIG. 1 illustrates a method for derivatizing a glass support, such as a Whatman GF/F glass fiber membrane, to provide support-bound amino groups. The glass fiber membrane is etched with acid, and then treated with aminopropyl-triethoxysilane (APTES) (Aebersold). The degree of amino group incorporation can be quantitated easily by ninhydrin assay. An exemplary protocol for derivatization of a glass support is provided in Example 1.

Figure 2:
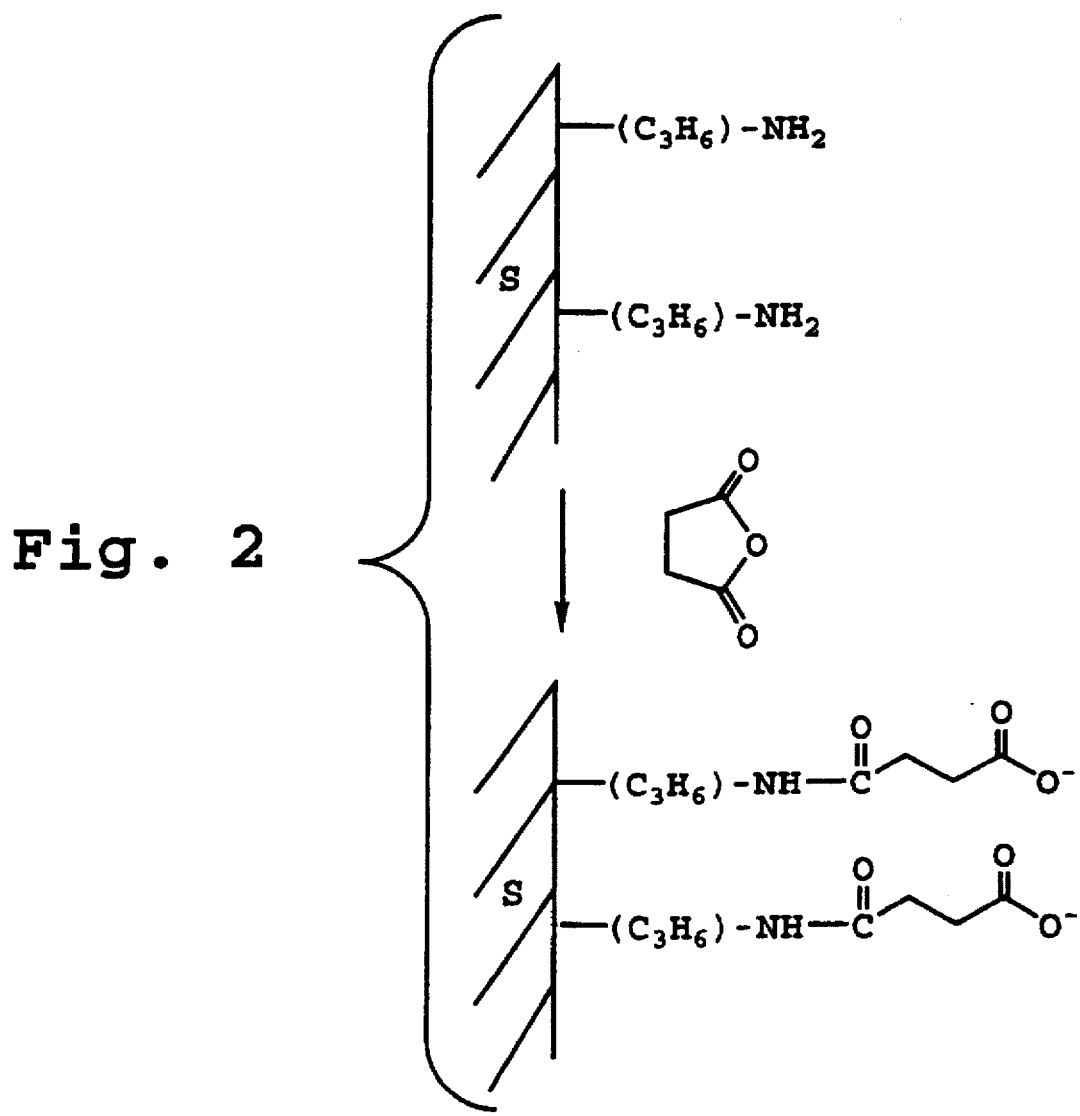
FIG. 2 illustrates conversion of support-bound amino groups to carboxylic acid groups by reaction with succinic anhydride.

Amino groups on the support described above, or on any other suitable support, can be converted to carboxylic acid groups by overnight incubation with succinic anhydride as illustrated in FIG. 2 and Examples 2 and 3. The time course of the reaction with succinic anhydride can be monitored by ninhydrin assay for residual amino groups.

The number of carboxylic acid groups on the support can be estimated by subtracting the number of amino groups on the support (ninhydrin assay) after succinic acid treatment from the number before treatment. Such analysis is useful for modifying reaction conditions to achieve a level of carboxyl groups on the support that is suitable for the particular needs of the user.

Many other methods can be used for incorporating carboxylic acid groups onto a solid support. For example, a poly(chlorotrifluoroethylene)-containing support can be modified to contain hydroxyl groups (Lee), which can be converted to carboxylic acid groups by reaction with succinic anhydride. Alternatively, the same support can be modified with 2-(lithiomethyl)-4,4-di-methyloxazoline, followed by reflux with a trifluoracetic acid/water/acetone mixture to introduce carboxylic acid groups directly onto the support (Dias).

B. Activating Reagent

In accordance with the invention, support-bound carboxylic acid groups are reacted with an N-substituted isoxazolium compound (Woodward et al.), such as 2-ethyl-5'-phenylisoxazoliumsulfonate (WRK), to form activated carboxylic acid groups (enol ester groups). The activated groups are derivatives of beta-acyloxy-N-ethylcinnamamide having an enol ester moiety (see bottom of FIG. 3), which is reactive with amino groups. In another specific embodiment, the N-substituted isoxazolium compound is Woodward's reagent L.

Figure 3:
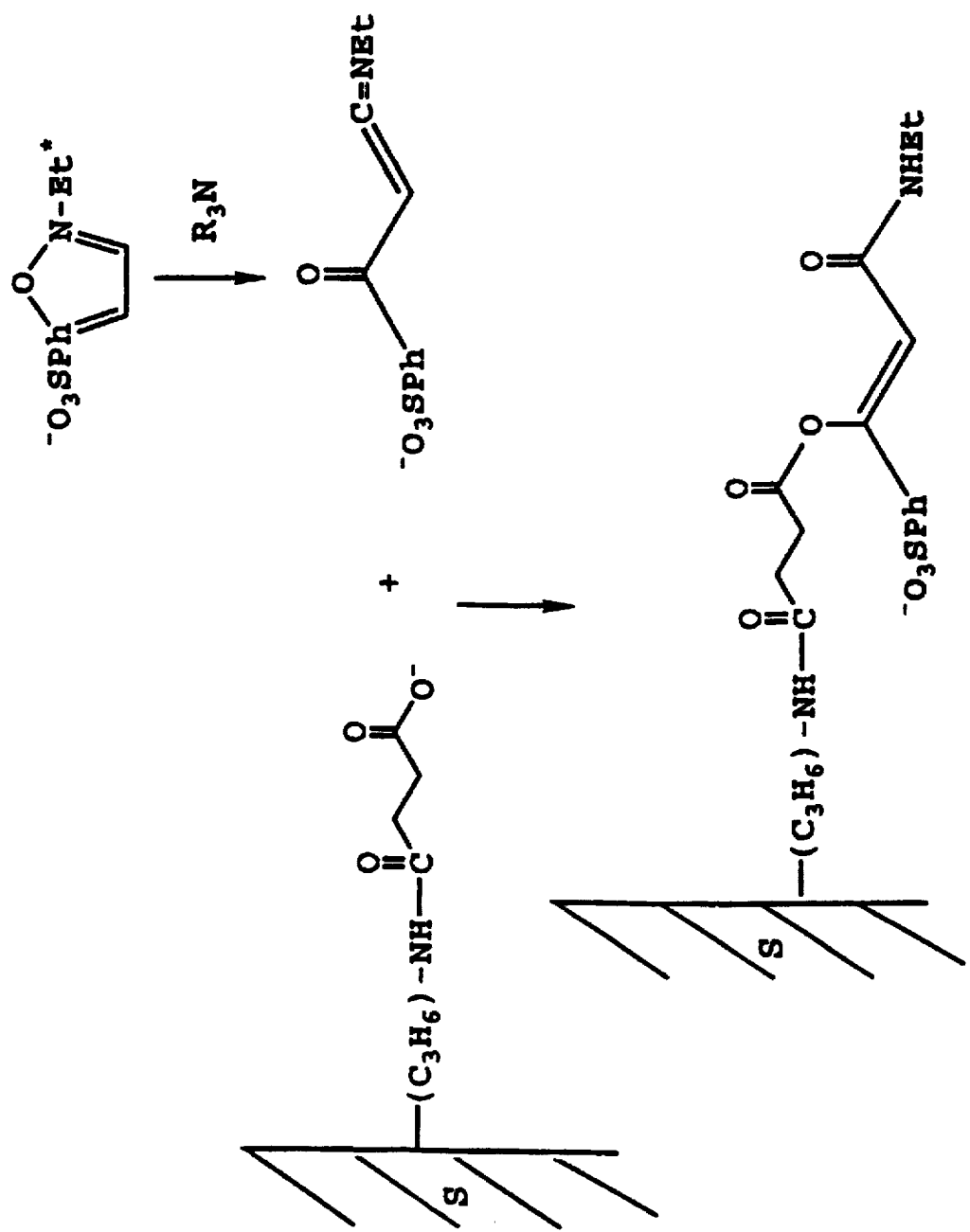
FIG. 3 illustrates conversion of support-bound carboxylic acid groups to activated carboxylate groups (enol ester groups) using Woodward's Reagent K (WRK)

Activation of carboxylic acid groups, illustrated in FIG. 3, is carried out in a suitable organic solvent, such as acetonitrile or N-methyl pyrrolidone, in the presence of suitable base such as diisopropylethylamine (DIEA), as described in Example 4. It can be appreciated that since the enol ester group is susceptible to nucleophilic attack by amines, the base used for catalyzing formation of the enol ester should be relatively non-nucleophilic. Tertiary amines, and particularly sterically hindered tertiary amines are thus preferred as the base.

Figure 4:
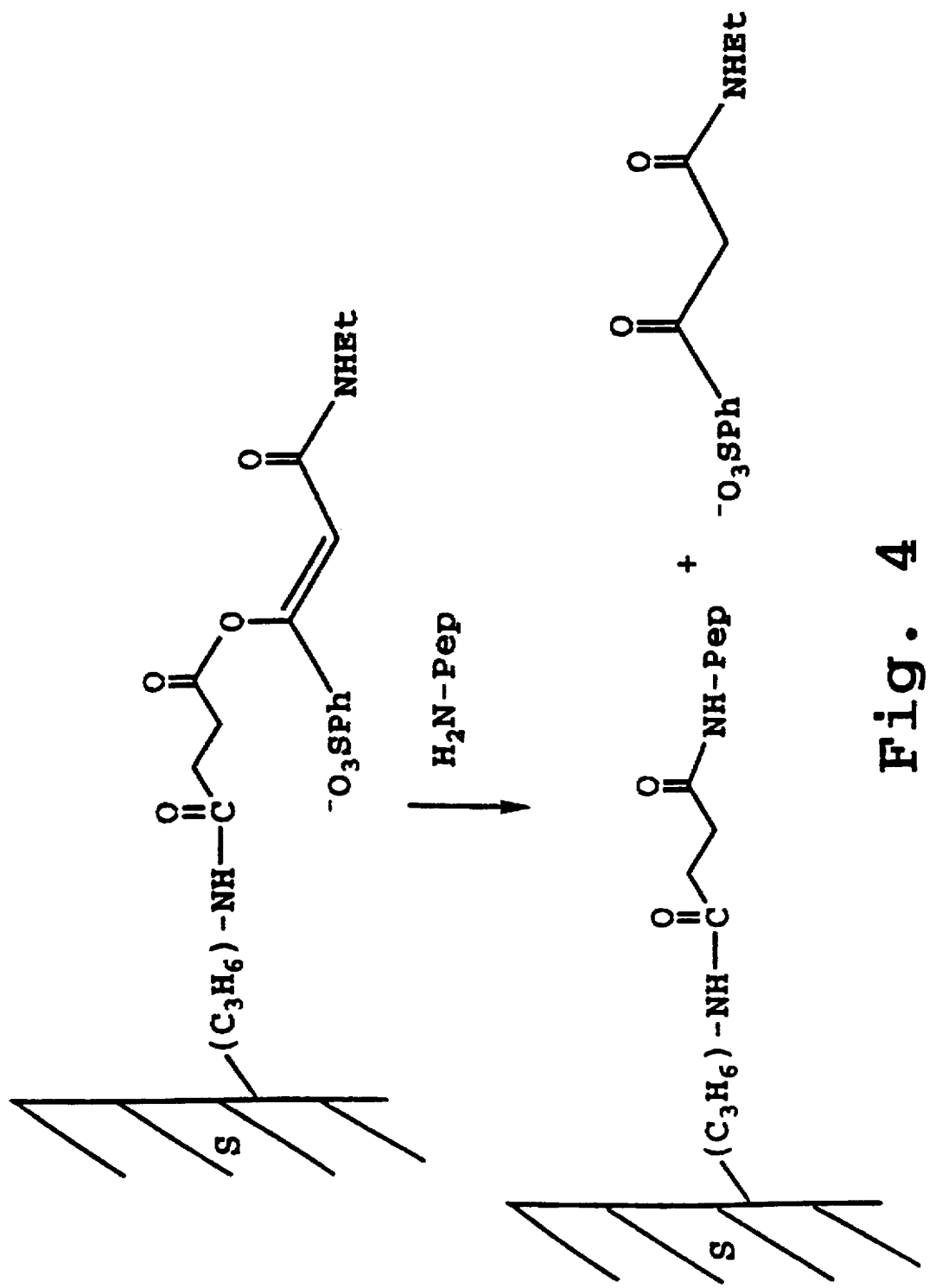
FIG. 4 illustrates peptide coupling to reactive support of the invention.
Figure 5A:
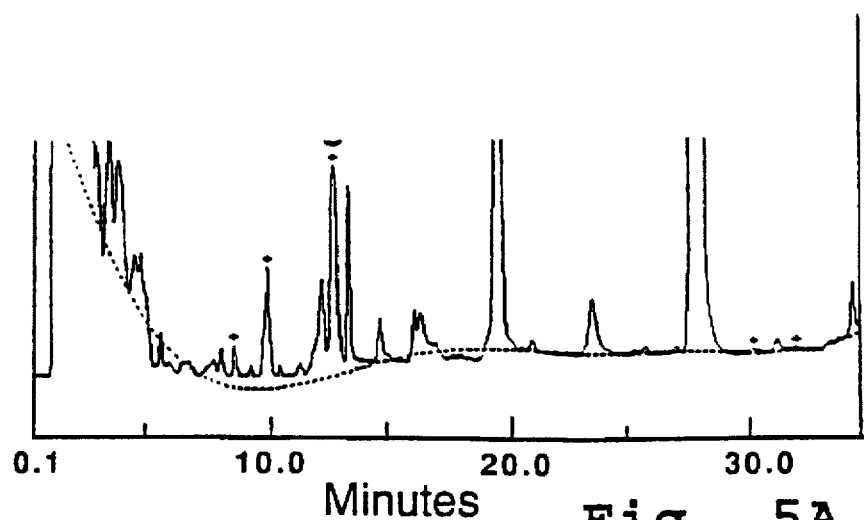
FIGS. 5A–5E illustrate HPLC chromatograms for first through fifth C-terminal sequencing cycles with apomyoglobin immobilized on a reactive support (PVDF-membrane) of the invention.
Figure 5B:
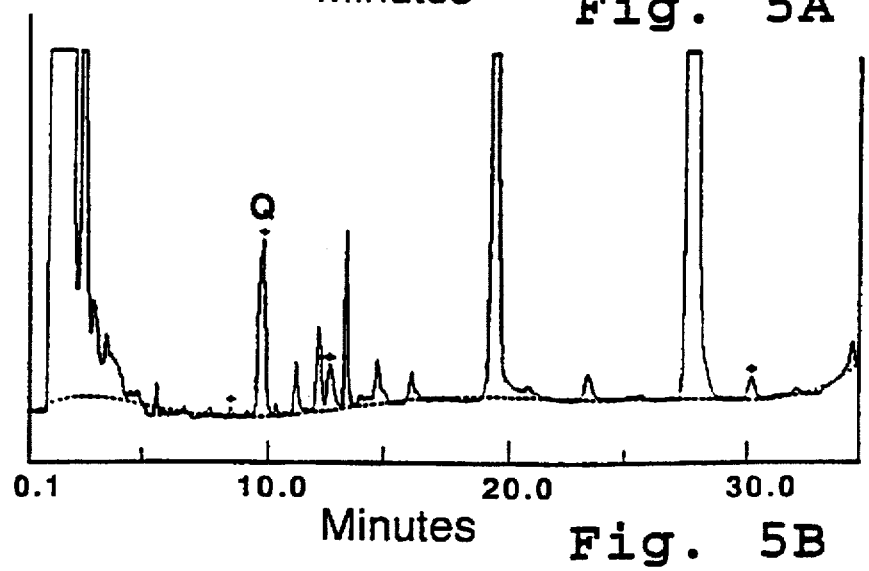
Figure 5C:
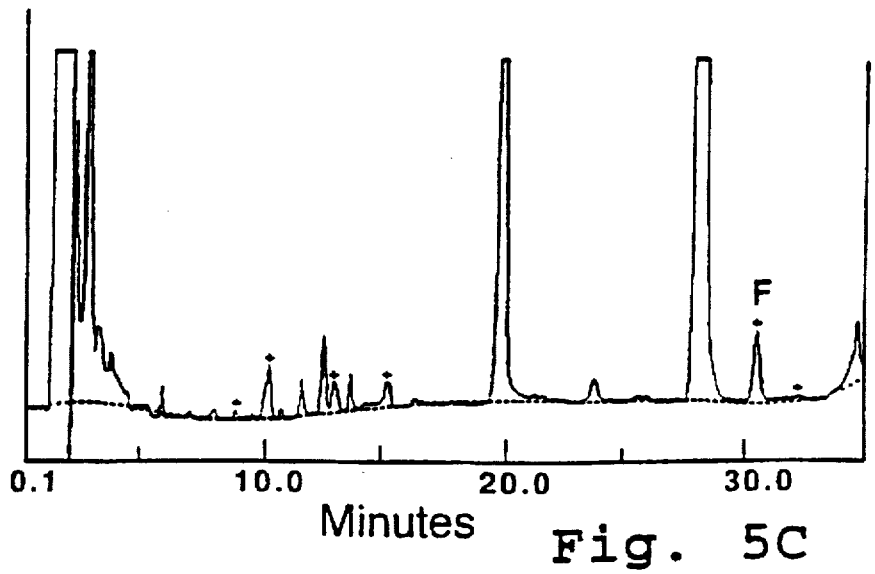
Figure 5D:
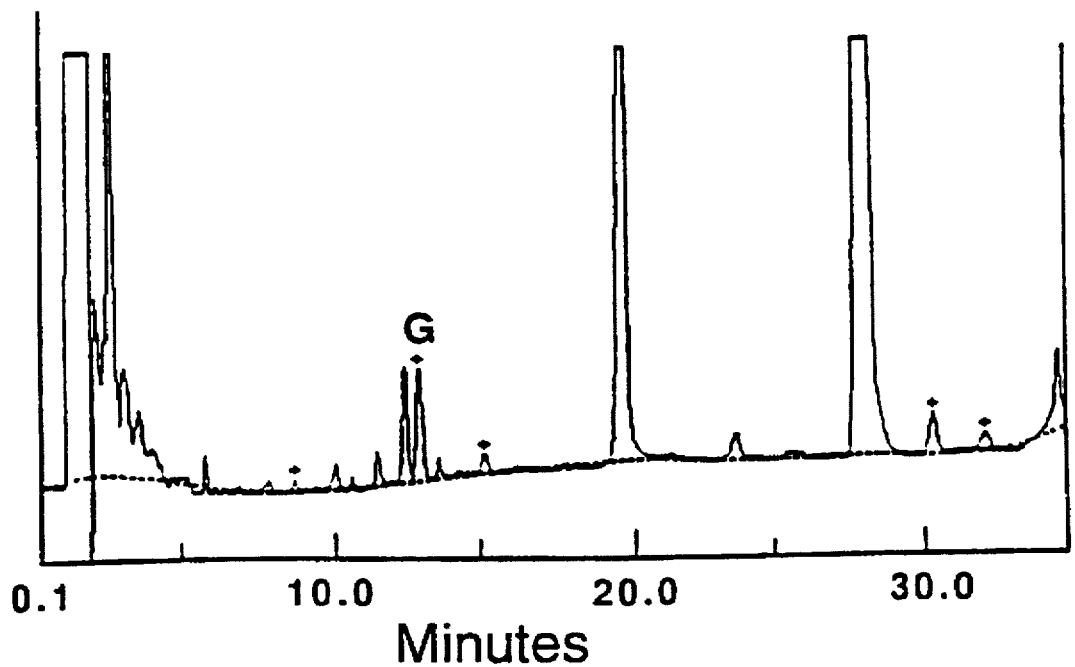
Figure 5E:
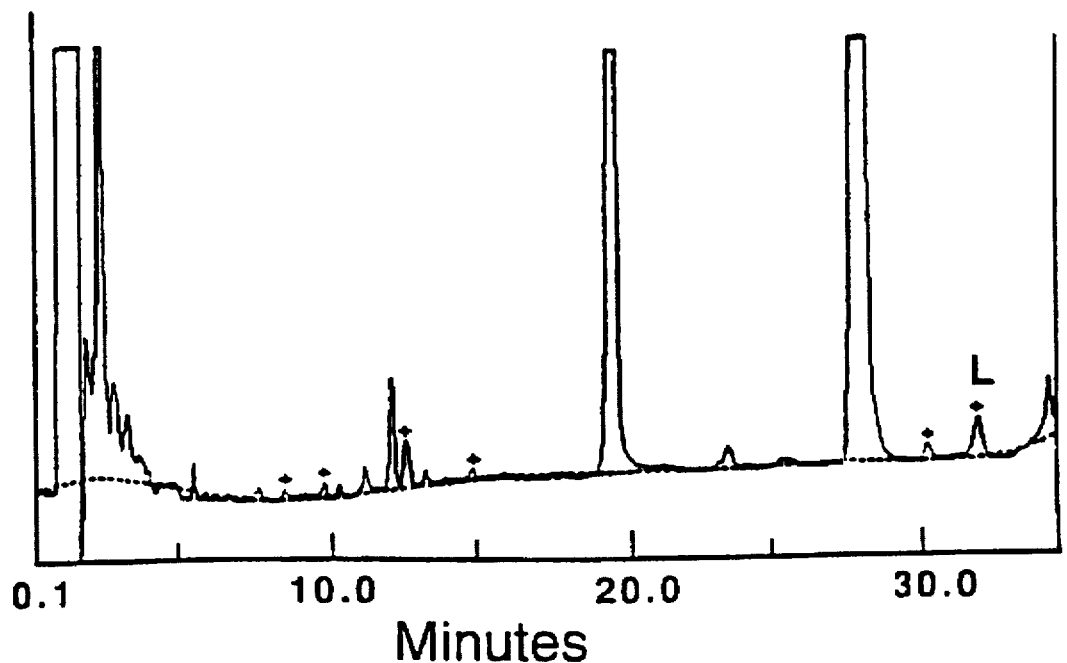
Figure 6A:
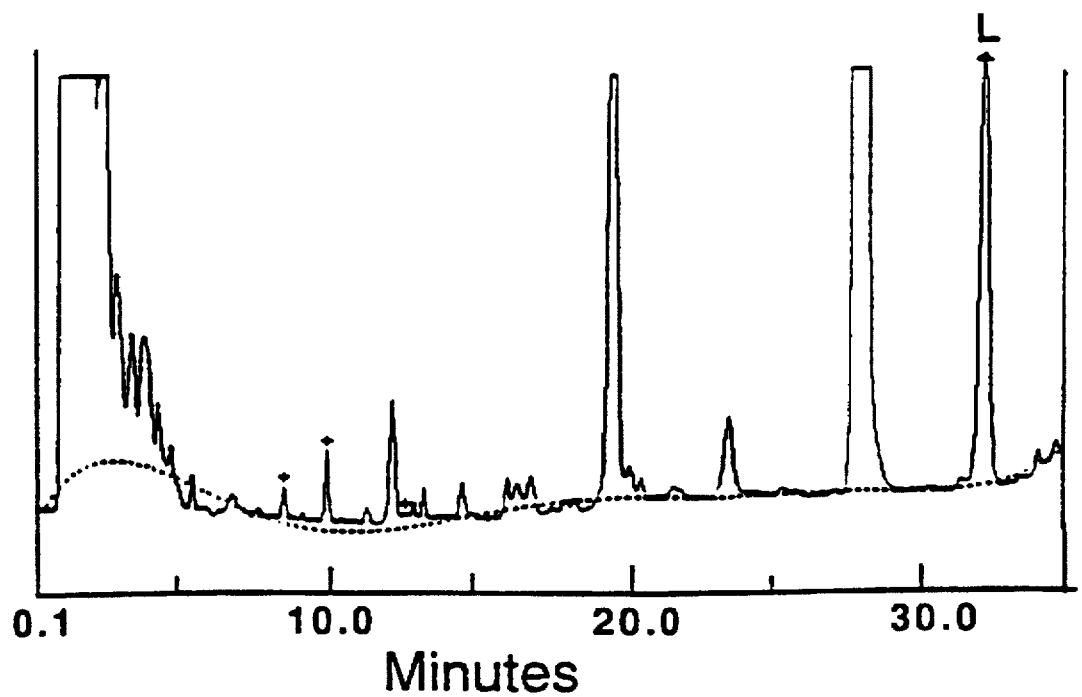
FIGS. 6A–6D illustrate HPLC chromatograms for first through fourth C-terminal sequencing cycles with lysozyme immobilized on a reactive support (activated PVDF-membrane) of the invention.
Figure 6B:
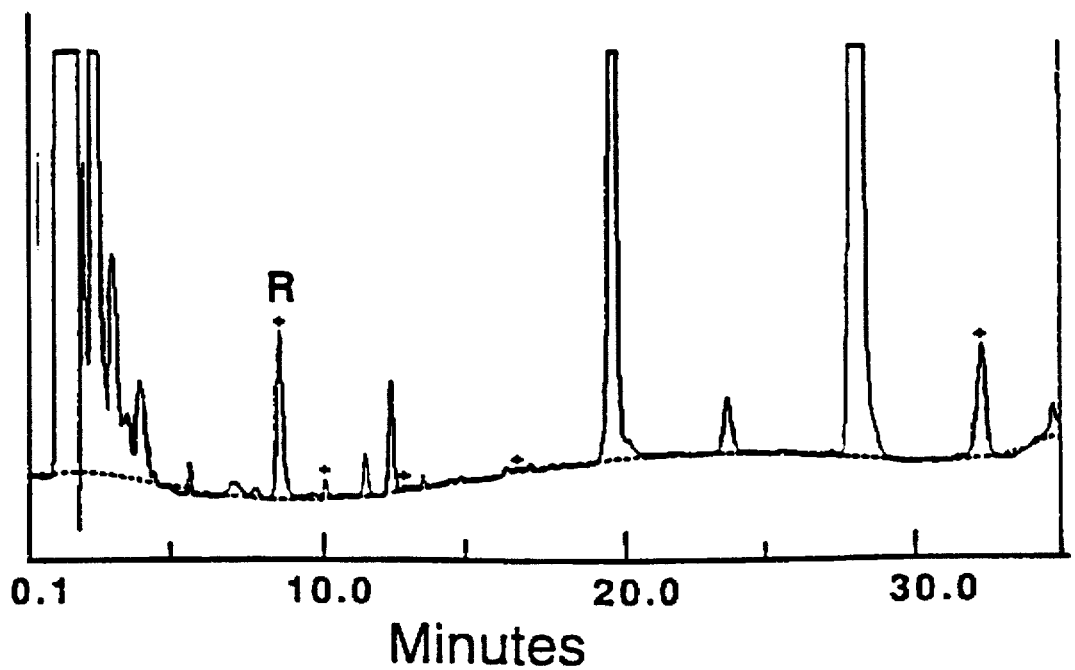
Figure 6C:
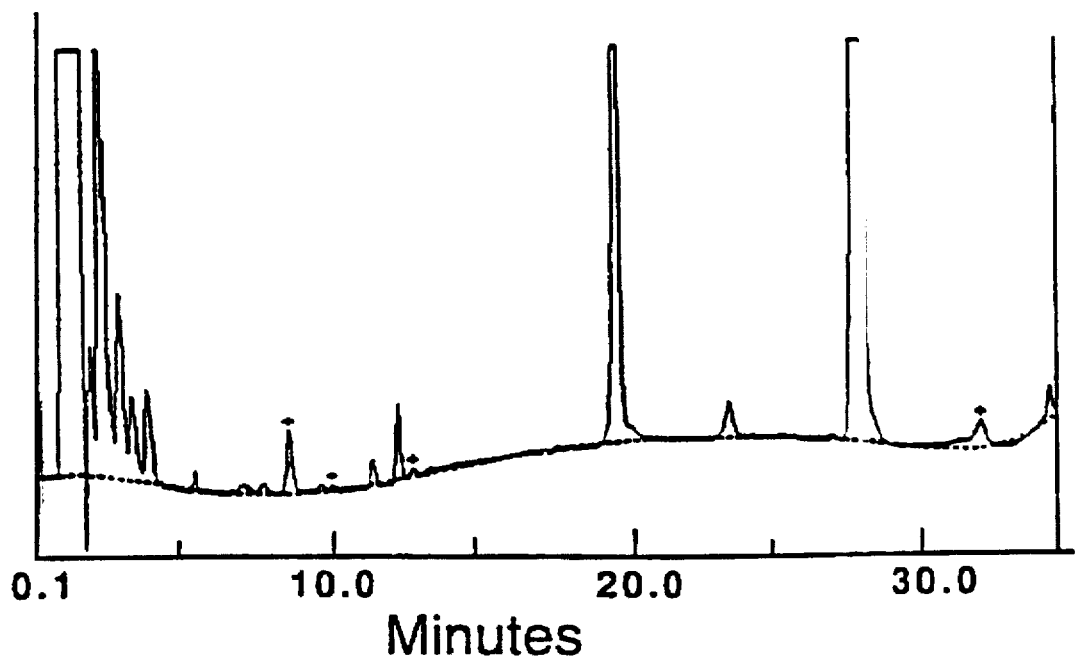
Figure 6D:
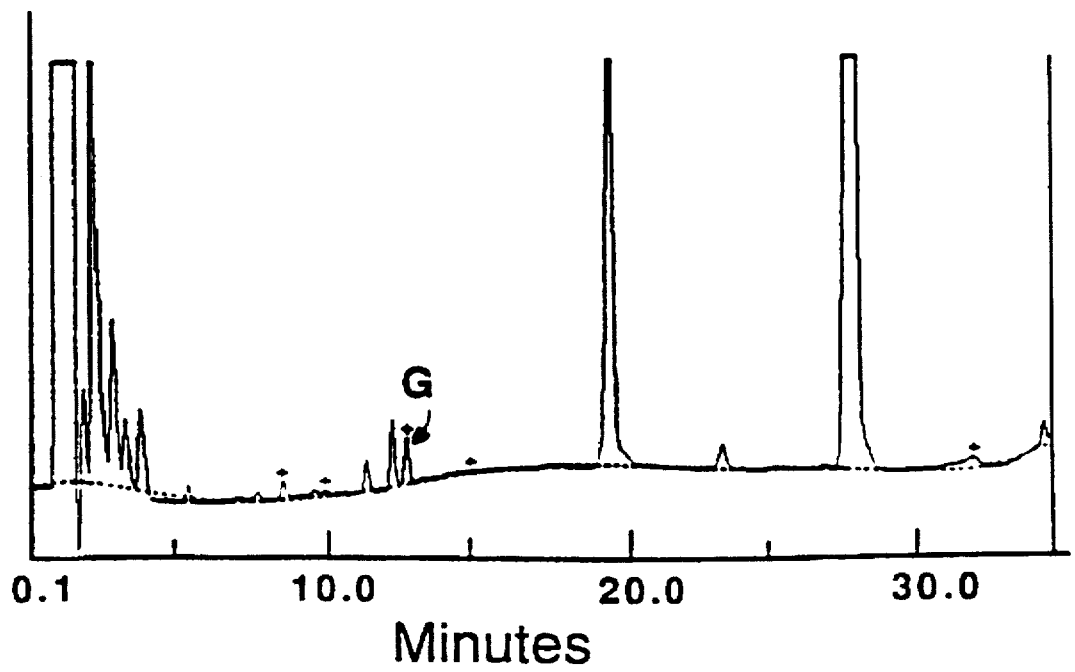
Figure 7A:
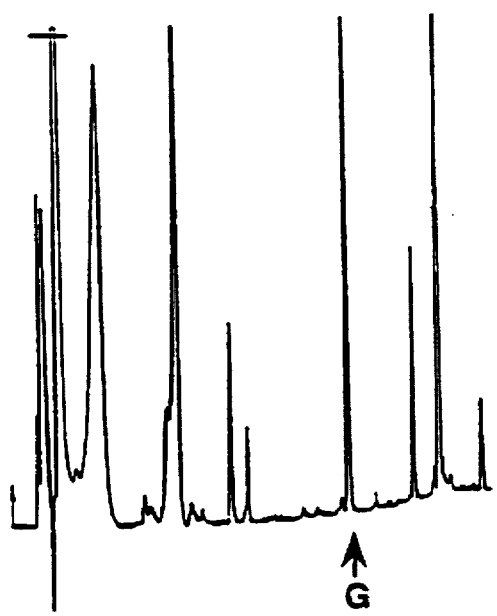
FIGS. 7A–7D illustrate HPLC chromatograms for first through fourth C-terminal sequencing cycles with a fifteen residue peptide (SEQ ID NO:1) immobilized on a reactive support (PVDF-membrane) of the invention.
Figure 7B:
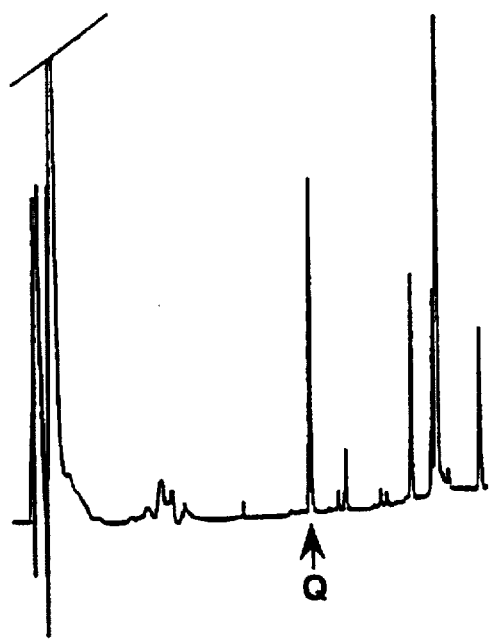
Figure 7C:
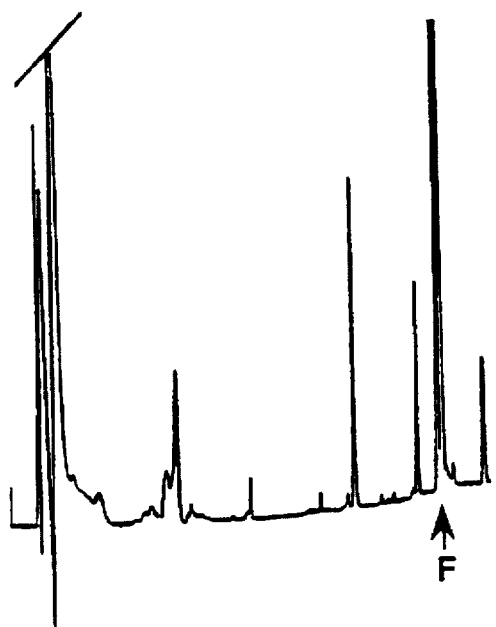
Figure 7D:
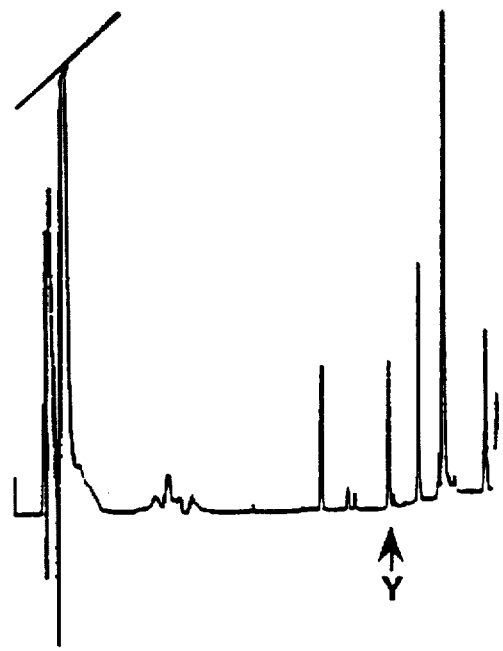
Figure 8A:
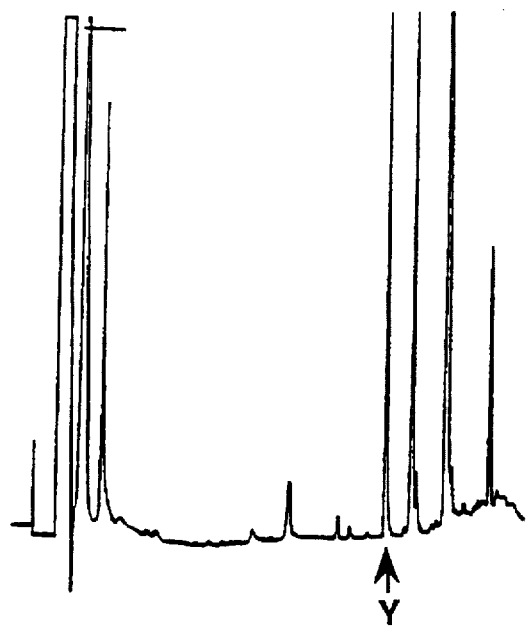
FIGS. 8A–8D illustrate HPLC chromatograms for first through fourth C-terminal sequencing cycles with a twelve residue peptide (SEQ ID NO:2) immobilized on a reactive support (polystyrene resin) of the invention.
Figure 8B:
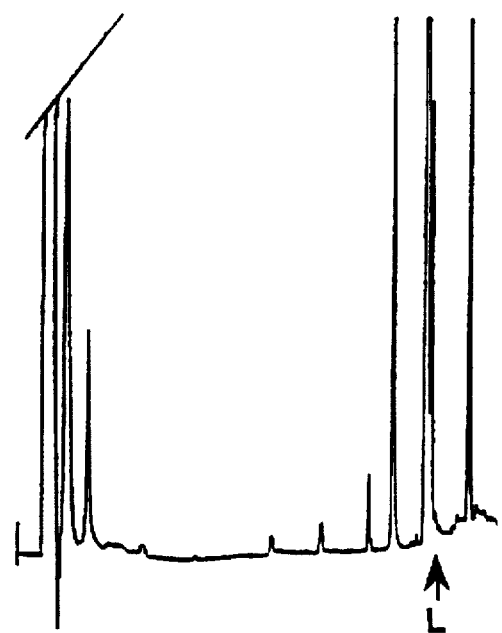
Figure 8C:
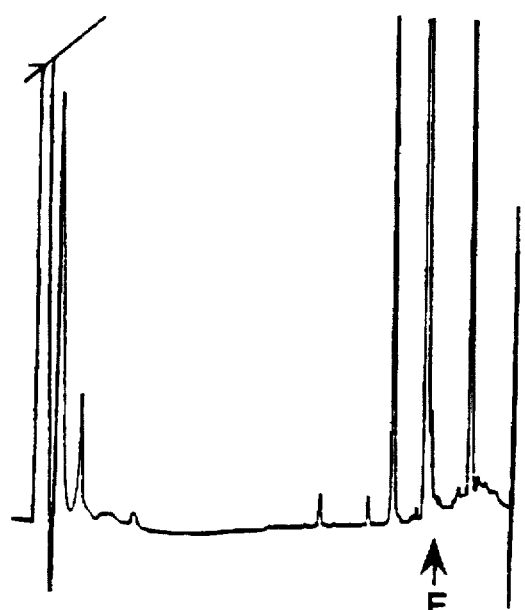
Figure 8D:
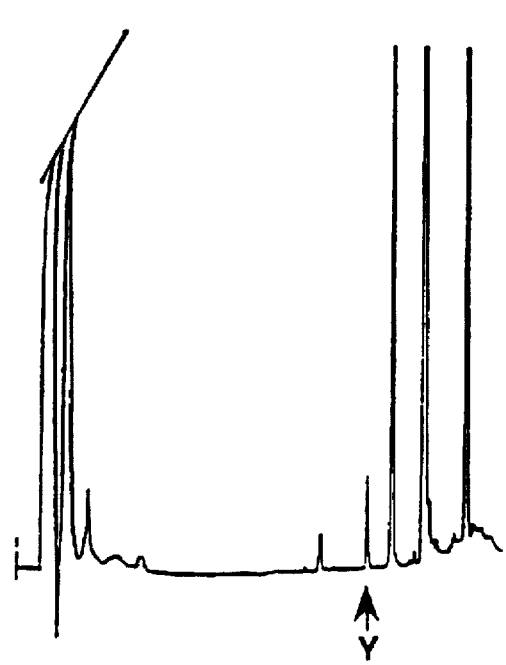
Figure 9A:
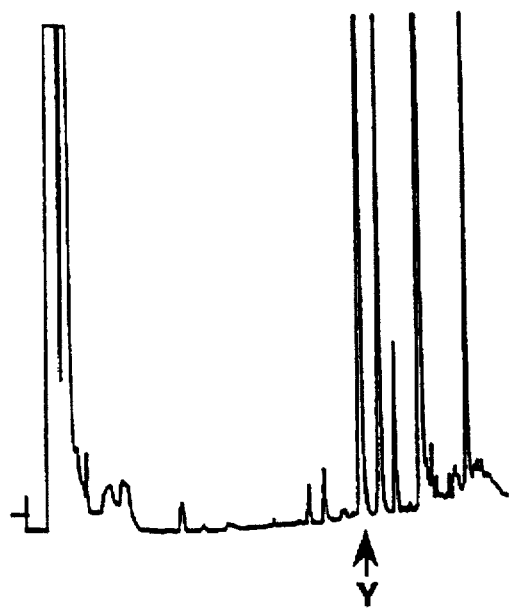
FIGS. 9A–9D illustrate HPLC chromatograms for first through fourth C-terminal sequencing cycles with a twelve residue peptide (SEQ ID NO:2) immobilized on a reactive support (CPG beads) of the invention.
Figure 9B:
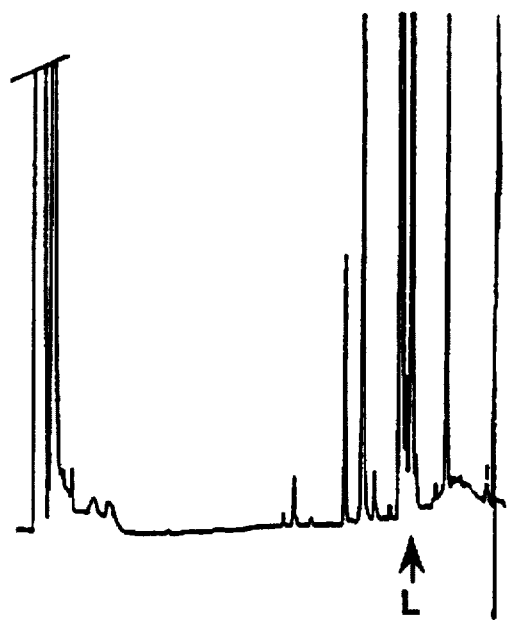
Figure 9C:
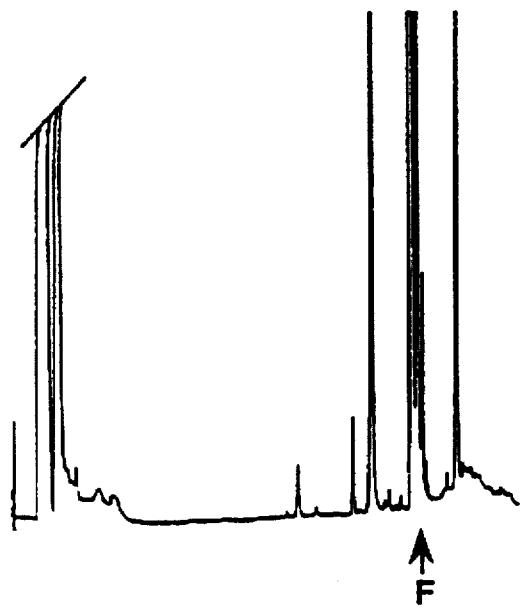
Figure 9D:
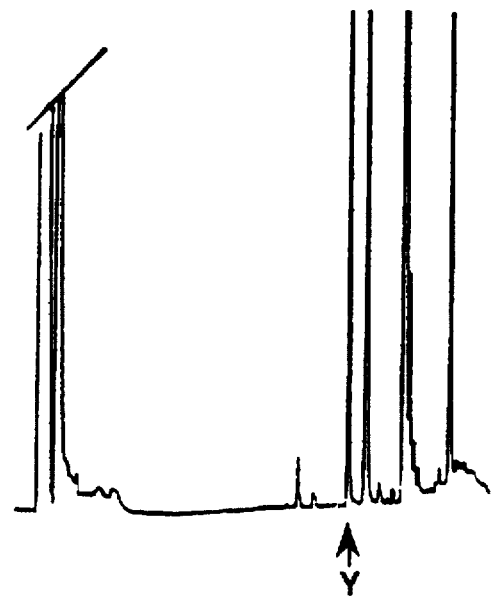
Figure 10A:
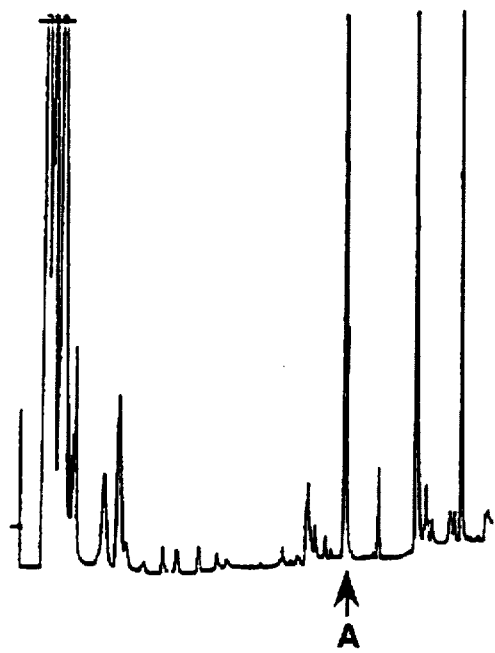
FIGS. 10A–10D illustrate HPLC chromatograms for first through fourth C-terminal sequencing cycles with an eleven residue peptide (SEQ ID NO:3) immobilized on a reactive support (CPG beads) of the invention, where immobilization was carried out in an organic solution.
Figure 10B:
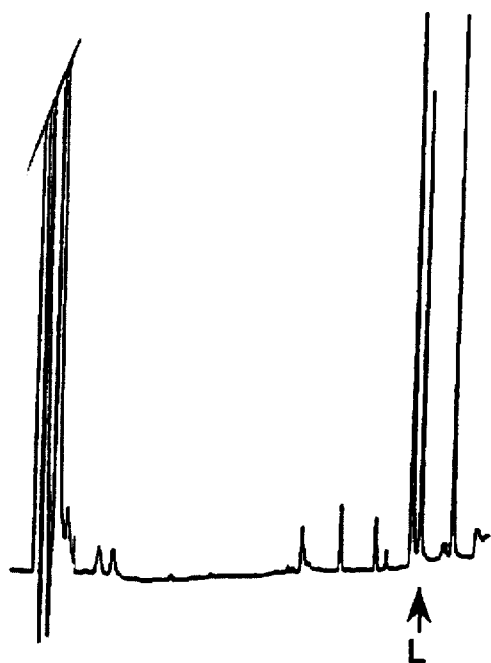
Figure 10C:
Figure 10D:
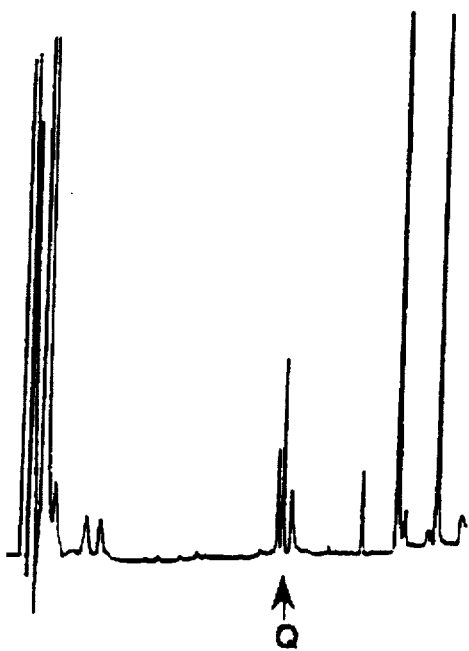
Figure 11A:
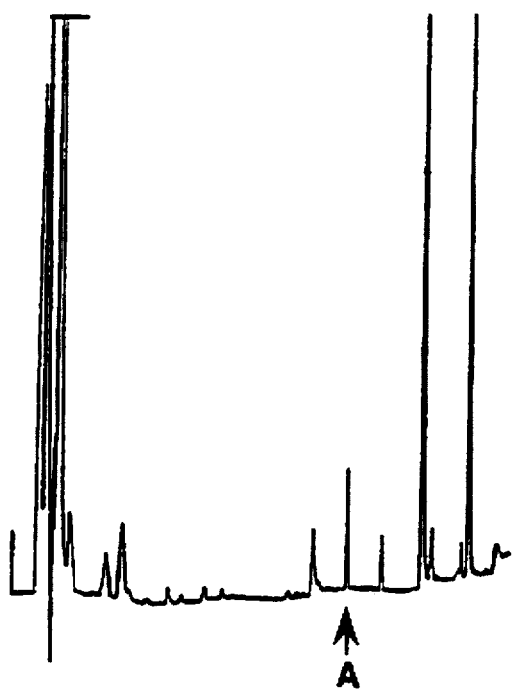
FIGS. 11A–11D illustrate HPLC chromatograms for first through fourth C-terminal sequencing cycles with the same peptide from FIGS. 10A–10D immobilized on a reactive support (DSS-derivatized CPG beads), where immobilization was carried out in an organic solution.
Figure 11B:
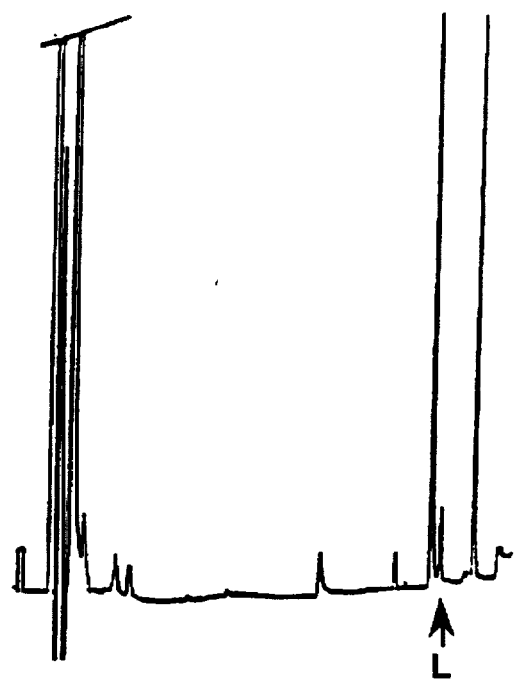
Figure 11C:
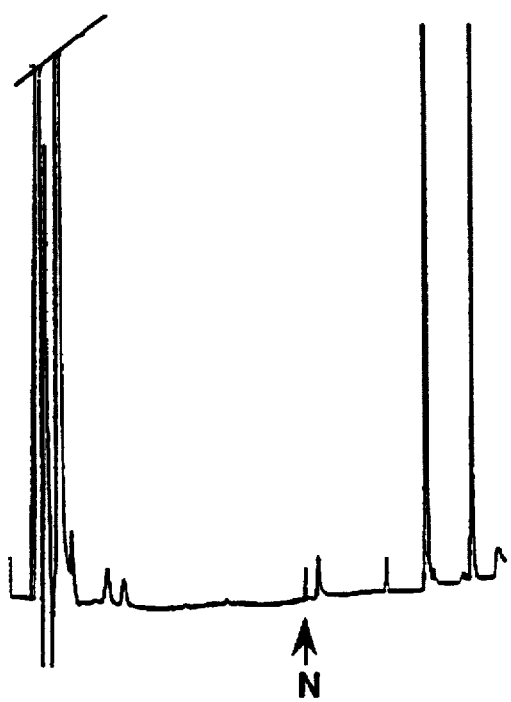
Figure 11D:
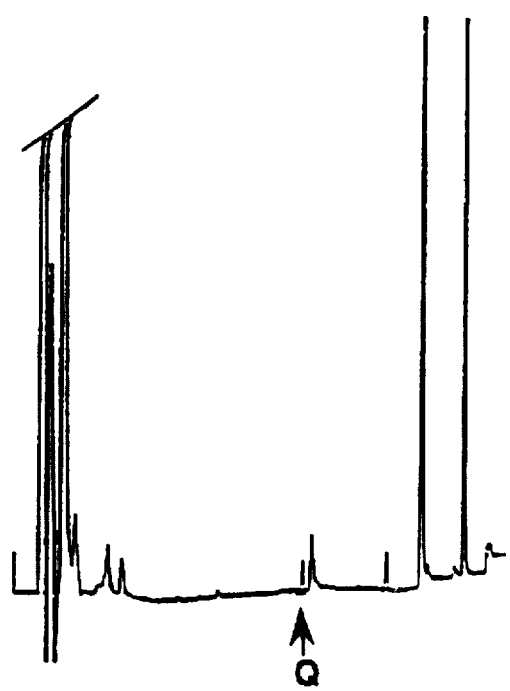
Figure 12A:
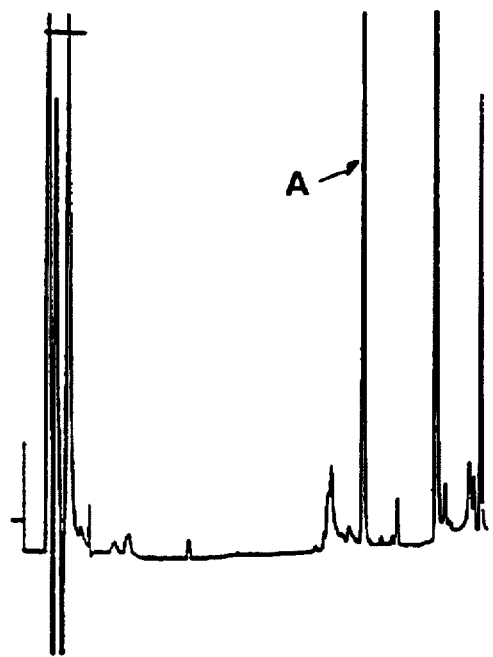
FIGS. 12A–12D illustrate HPLC chromatograms for first through fourth C-terminal sequencing cycles with the peptide and reactive support from FIGS. 10A–10D, where immobilization was carried out in an aqueous solution at pH 6.
Figure 12B:
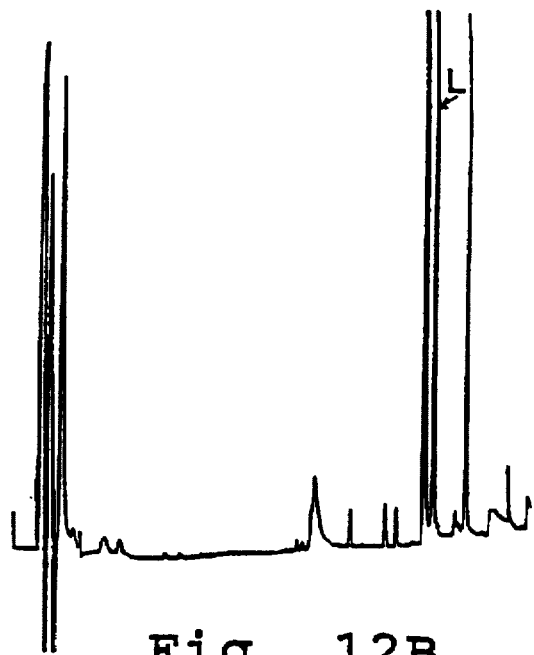
Figure 12C:
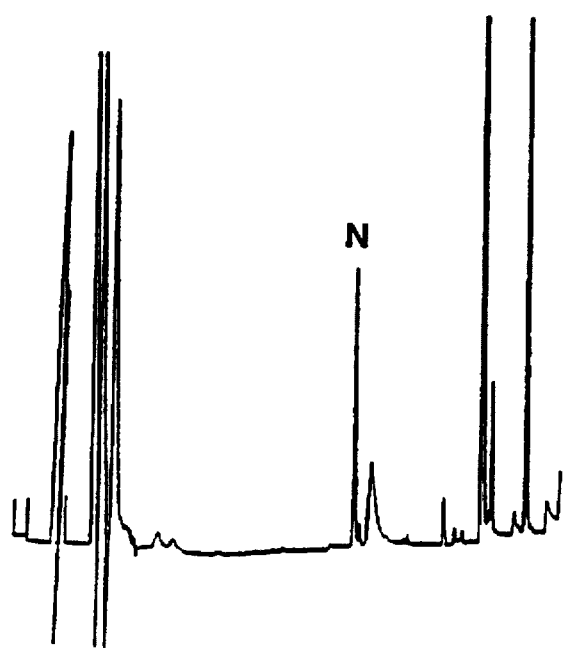
Figure 12D:
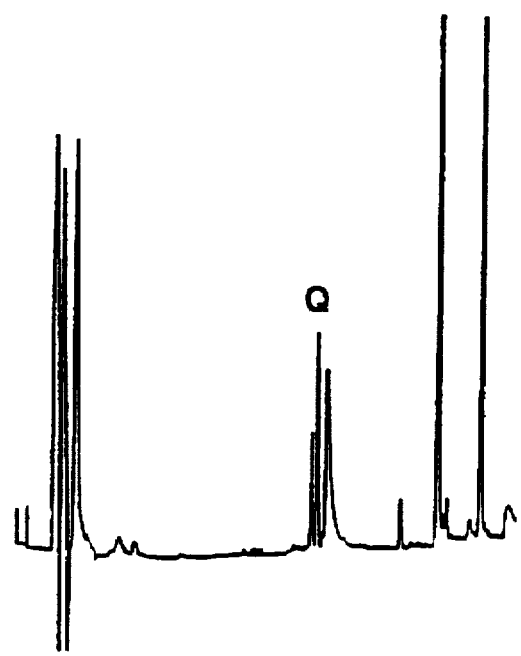

As illustrated in FIG. 3, the carboxylic acid-containing support can be activated using WRK in the presence of base (preferably non-nucleophilic as above) to generate a reactive ketenimine intermediate in situ (Woodward). The reactive ketenimine reacts readily with the support-bound carboxylic acid groups to form an enol ester group, as shown in FIG. 4. This reaction can be carried out by immersing a carboxylated support in a solution containing WRK and base, as detailed in Example 4.

For example, a glass fiber membrane that contains support-bound carboxylic acid groups can be placed in a shallow dish with a freshly prepared ketenimine solution which is gently swirled for about 4–6 hours. The membrane is then washed with acetonitrile to remove unreacted ketenimine, and the activated support is allowed to air-dry. A number of activated supports prepared in this manner have been found by the inventors to be stable over an extended period of time and can be stored at room temperature for months prior to use for peptide immobilization (Example 9).

C. Peptide Immobilization

For covalent attachment to an activated support of the invention, a polypeptide is dissolved in a buffered aqueous solution or an organic solvent and contacted with the activated support for a time sufficient for the polypeptide to become immobilized on the support.

According to an important aspect of the invention, the inventors have found that the dried, activated support is compatible with sample loading under aqueous conditions over a broad pH range; that is, covalent attachment of the polypeptide to the support can be carried out under aqueous conditions, without significant hydrolysis (i.e., inactivation) of support-bound enol ester groups by water.

In studies conducted in support of the invention, several solid supports containing or derivatized to contain carboxylic groups were activated using WRK, and the activated supports were tested for their ability to immobilize proteins. In addition, peptide immobilization with WRK-activated supports were compared with other peptide immobilization methods, as described below.

C.1. Polypeptide Immobilization

For immobilization of polypeptides (proteins and peptides) on the activated solid supports of the invention, the polypeptide may be dissolved in an organic solvent, with an ion-pairing agent if necessary (e.g., trifluoroacetic acid), or alternatively, the polypeptide may be dissolved in a buffered aqueous solution with a pH of about 1 to about 8.

To assure the highest degree of polypeptide immobilization on the support, the activated support may be immersed in the polypeptide solution and incubated for several hours at room temperature. For faster immobilization, an aliquot of polypeptide solution may be spotted onto the support and then allowed to dry (e.g., Example 15A).

Where the support takes the form of a membrane in a spin-filtration device, immobilization can be effected by centrifugation, where polypeptide is retained by the support as the solution is forced centrifugally through the support. For example, the membrane can be configured as an insert which can be suspended from the mouth of a centrifuge tube (Example 15B). Sample polypeptide solution is placed in the insert, and the centrifuge tube/insert assembly is centrifuged for time sufficient to pass all of the solution through the membrane, leaving the polypeptide immobilized on the membrane.

After the polypeptide has been immobilized on the activated support, the support is typically washed a few times to remove unbound polypeptide prior to sequence analysis. Note that high temperatures or strongly basic conditions should be avoided to minimize de-activation of the support.

FIGS. 5A–5E and 6A–6D show HPLC chromatograms from C-terminal sequence analysis of apomyoglobin and lysozyme. These proteins were immobilized at pH 7 on WRK-activated PVDF membranes by the procedures described in Examples 5 and 6. With reference to FIGS. 5A–5E, the apomyoglobin sample was readily sequenceable through the fifth residue. Similarly, FIGS. 6A–6D show that the first four C-terminal residues in lysozyme were readily sequenced. Note that for lysozyme, no peak was observed in the third sequencing cycle (FIG. 6C) presumably because the third-in residue, cysteine, remains disulfide-bonded to another cysteine residue in the lysozyme polypeptide chain and thus cannot be released as a free thiohydantoin derivative.

Figure 17:
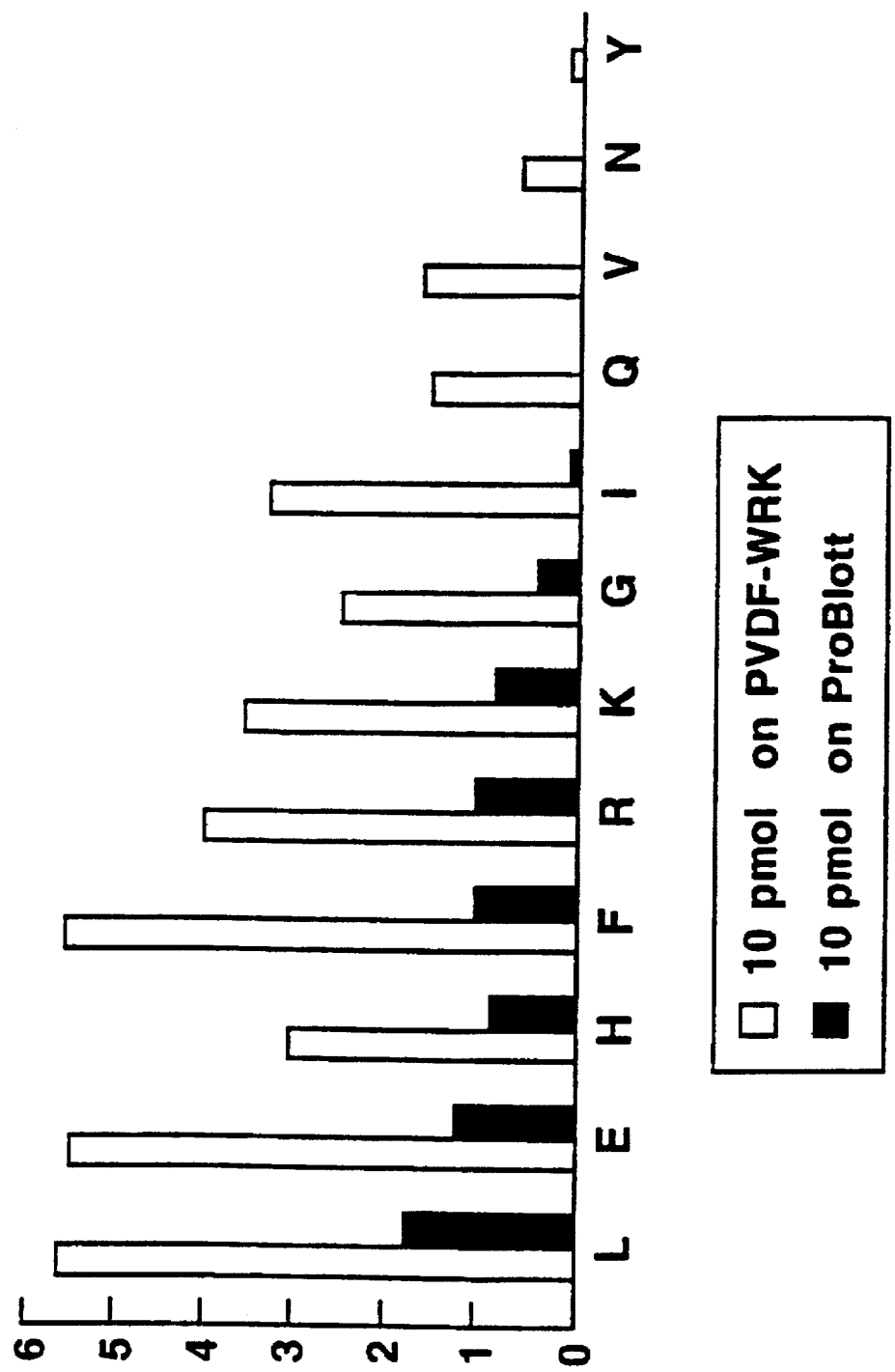
FIG. 17 shows a plot of reaction yield versus sequencing cycle for N-terminal sequencing of a twelve residue peptide (SEQ ID NO:4) immobilized on a reactive support (PVDF membrane) of the invention (hollow bars), and on a non-carboxylated, non-activated PVDF membrane (solid bars)

FIGS. 7A–7D and 9A–9D show HPLC chromatograms from C-terminal sequencing (Example 14) of small peptides. For peptides that are poorly soluble in water, immobilization can be carried out in an organic solvent such as dimethylformamide (DMF), N-methyl pyrrolidone (NMP), or acetonitrile. However, for water-soluble peptides, high immobilization yields can be attained in aqueous media as well. In general, the concentration of peptide may be 1 to 6 mg/ml to expedite polypeptide immobilization, although lower concentrations may be used. FIG. 17, for example, shows N-terminal sequence analysis of just 10 pmol (spotted on the membrane) of a 12 residue peptide.

FIGS. 7A–7D show C-terminal sequence analysis of a 15 residue peptide (SEQ ID NO:1) which had been immobilized on a WRK-activated PVDF-membrane (Example 7). As can be seen from the figures, strong signals for the alkylated thiohydantoin peaks were observed in all four sequencing cycles.

FIGS. 8A–8D show C-terminal sequence analysis of a 12 residue peptide (SEQ ID NO:2) which had been immobilized on a WRK-activated polystyrene resin prepared by the general procedures described in Examples 3 and 4. In this example, the amount of support-bound amino groups that were present prior to succinic anhydride modification was determined to be approximately 26 μmol/g of resin, as determined by ninhydrin assay. After derivatization with succinic anhydride, no free amino groups could be detected, suggesting that the amino groups had been converted quantitatively to carboxylic acid groups. As can be seen from FIGS. 8A–8D, strong alkylated thiohydantoin peaks were observed in all four sequencing cycles.

FIGS. 9A–9D show C-terminal sequence analysis of the same 12 residue peptide that was used in FIGS. 8A–8D, but immobilized on WRK-activated CPG beads (prepared as described in Examples 3 and 4). Again, strong sequencing peaks were observed through the first four sequencing cycles shown.

C.2 Comparison With DSS-Activated Support

In experiments conducted in support of the invention, immobilization yields using WRK-activated support were compared with yields obtained with other peptide immobilization methods.

In one study, the immobilization yields of WRK-activated CPG beads prepared as described in Examples 3 and 4 were compared with yields afforded by CPG beads activated with disuccinimidyl suberate (DSS). DSS is a bifunctional cross-linking reagent (available from Pierce, Rockford, Ill.) that has been used for coupling polypeptide amino groups to amine-derivatized supports. Preparation of the DSS-derivatized beads used in the study is described in Example 8.

The two activated supports were tested by immobilizing a synthetic 11 residue peptide (SEQ ID NO:3, "11-mer") onto each support by procedures described above. In one set of experiments, polypeptide immobilization was carried out in an organic solvent, N-methyl pyrrolidone (NMP). In a second set of experiments, immobilization was carried out in 0.1M phosphate buffer, pH 6. Comparative immobilization yields were determined by inspection of the amplitudes of the HPLC peaks for the amino acid alkylated thiohydantoin derivative released at the end of each sequencing cycle.

FIGS. 10A–10D and 11A–11D show HPLC chromatograms from the first four C-terminal sequencing cycles for peptide bound to WRK-activated CPG beads (FIGS. 10A–10D) and DSS-activated CPG beads (FIGS. 11A–11D), where immobiliziation of the 11-mer was carried out in NMP. As can be seen, the WRK-activated beads afforded larger thiohydantoin peaks than did the DSS-activated beads, indicating that the WRK-activated CPG beads had bound a greater amount of 11-mer (that is, a greater immobilization yield) than had the DSS-activated beads.

Figure 13A:
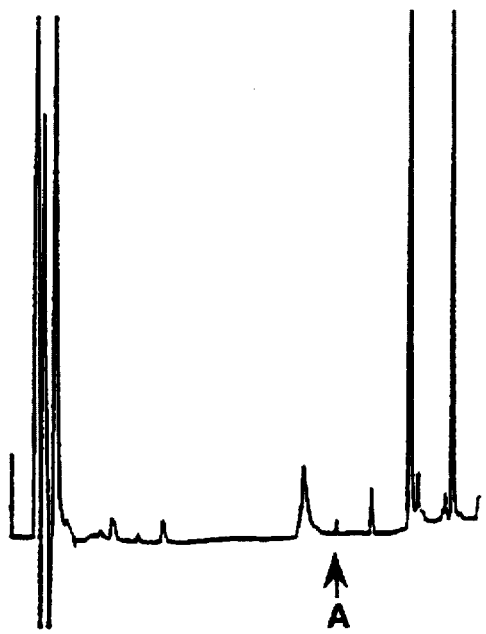
FIGS. 13A–13C illustrate HPLC chromatograms for first through third C-terminal sequencing cycles with the peptide and reactive support (DSS-derivatized CPG beads) from FIGS. 11A–11D, where immobilization was carried out in aqueous solution at pH 6.
Figure 13B:
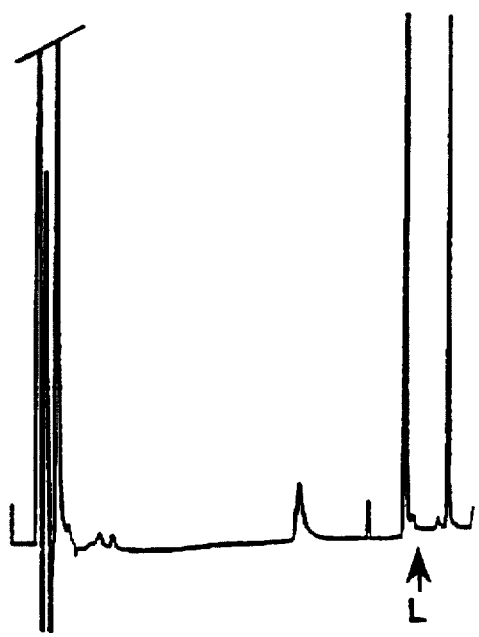
Figure 13C:
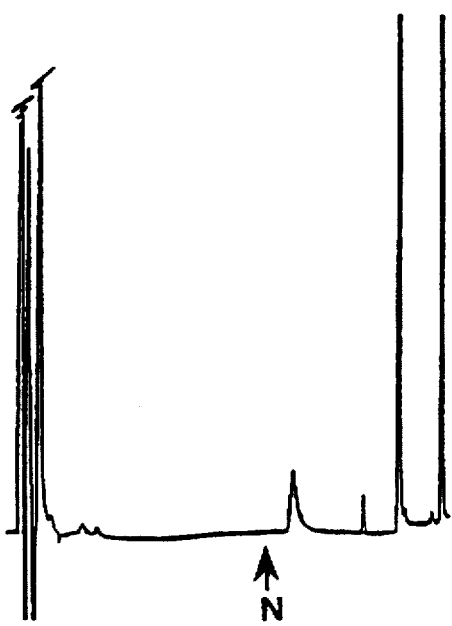
Figure 14A:
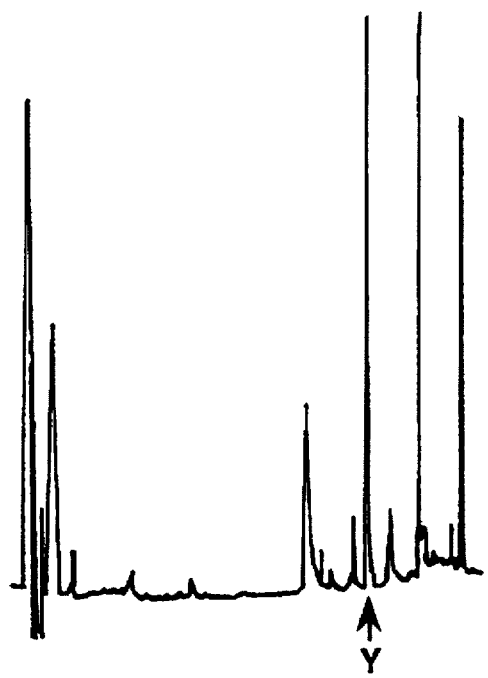
FIGS. 14A–14D show HPLC chromatograms for first through fourth C-terminal sequencing cycles with a twelve residue peptide (SEQ ID NO:2) immobilized on a reactive support (polystyrene) which had been stored in dried form for 3 months prior to use.
Figure 14B:
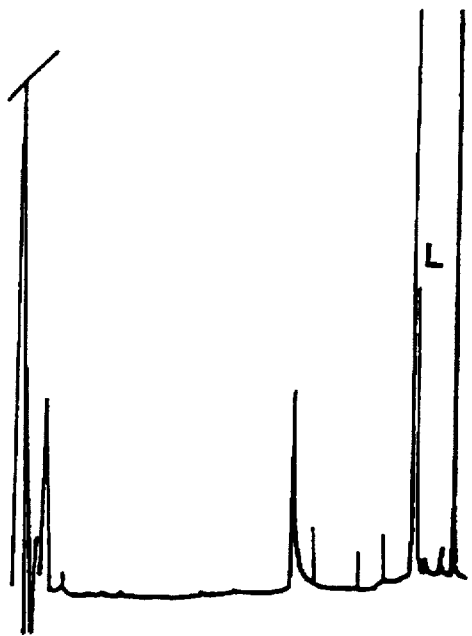
Figure 14C:
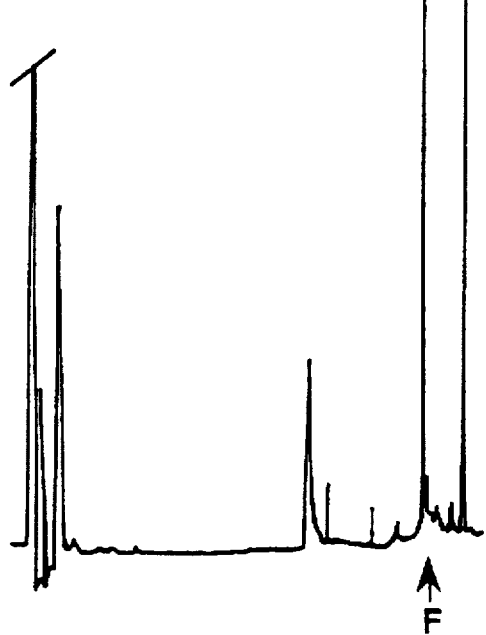
Figure 14D:
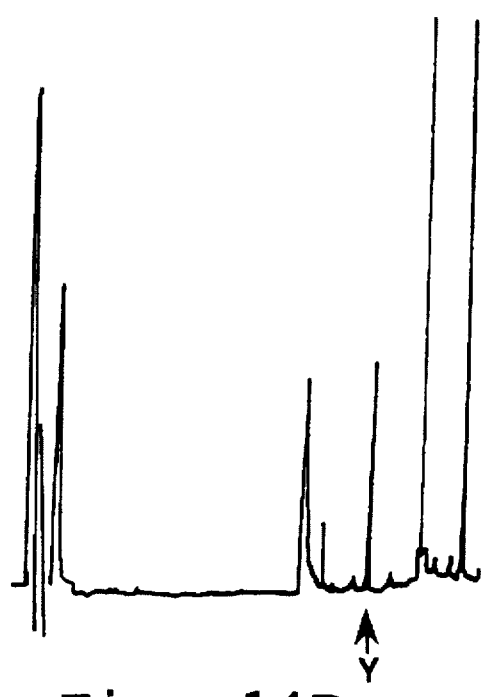
Figure 15A:
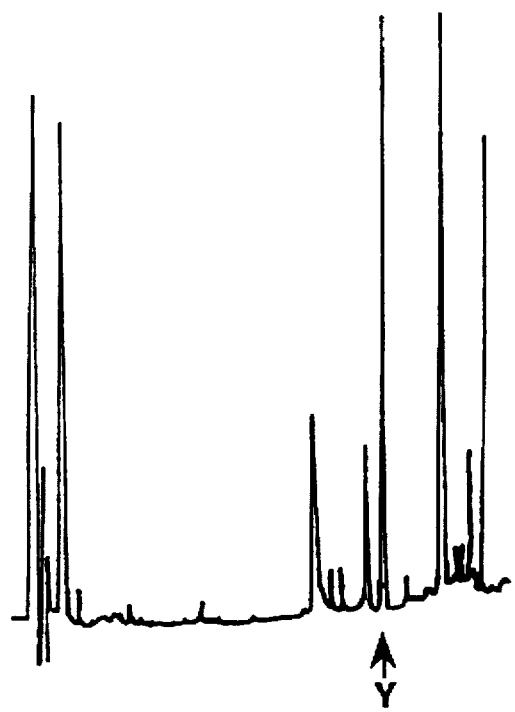
FIGS. 15A–15D show HPLC chromatograms for first through fourth C-terminal sequencing cycles with a twelve residue peptide (SEQ ID NO:2) immobilized on a reactive support (CPG beads) which had been stored in dried form for 6 months prior to use.
Figure 15B:
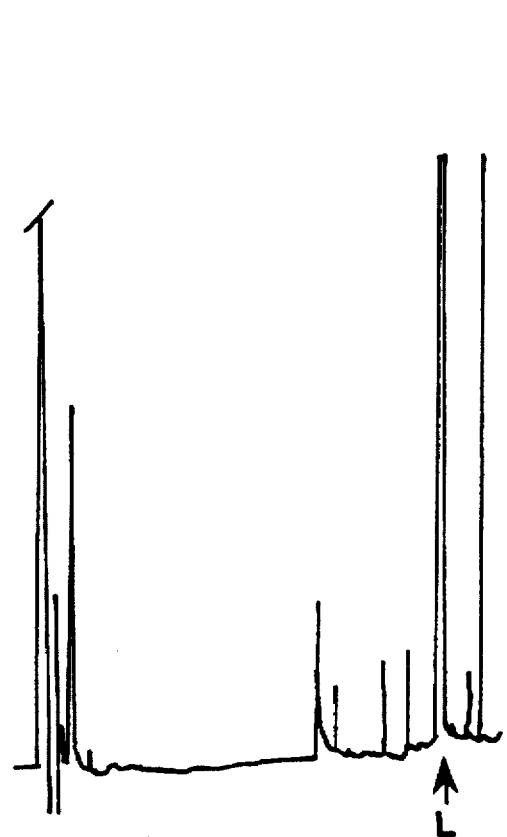
Figure 15C:
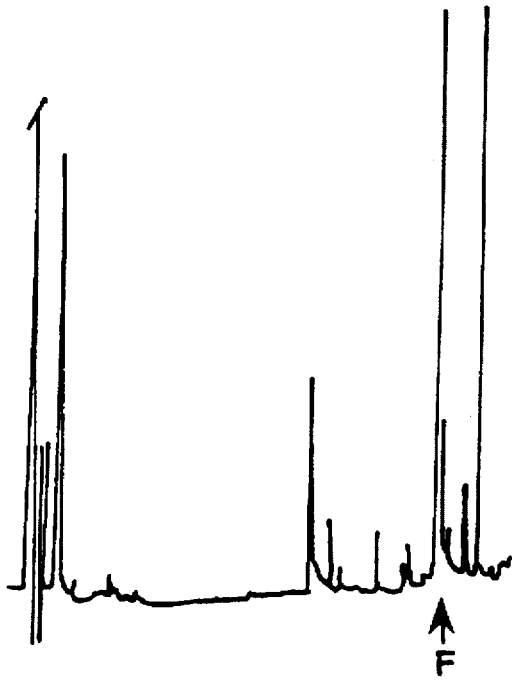
Figure 15D:
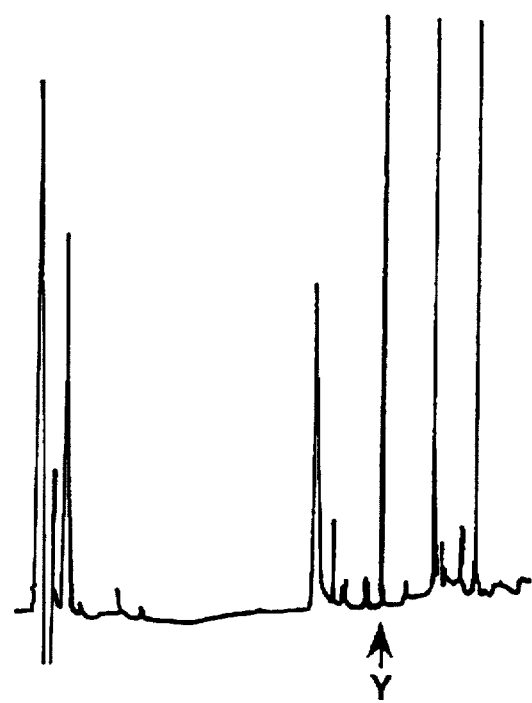
Figure 16A:
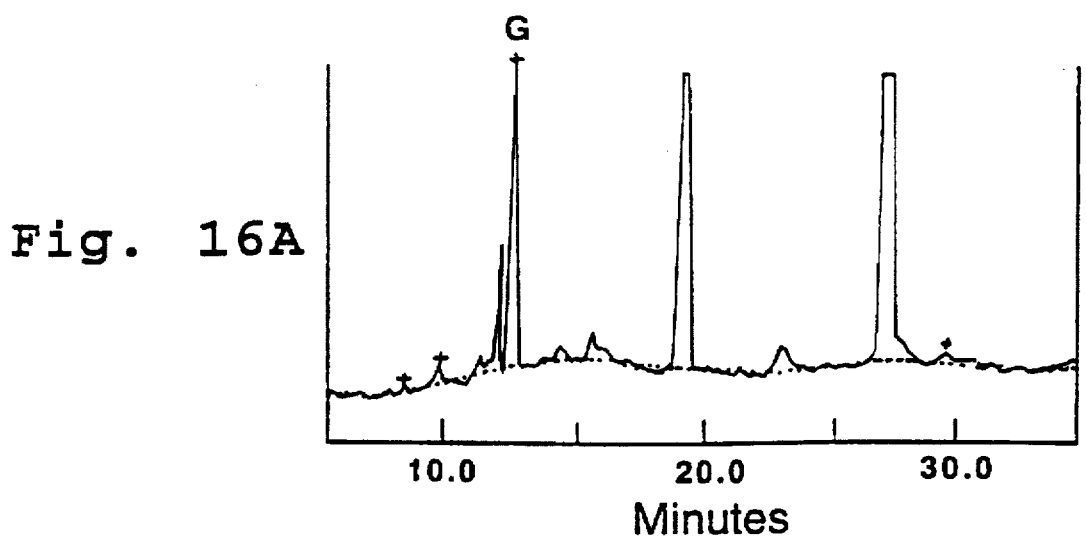
FIGS. 16A–16E show HPLC chromatograms for first through fifth C-terminal sequencing cycles with apomyoglobin immobilized on a reactive support (PVDF membrane) which had been stored in dried form for 3 months prior to use.
Figure 16B:
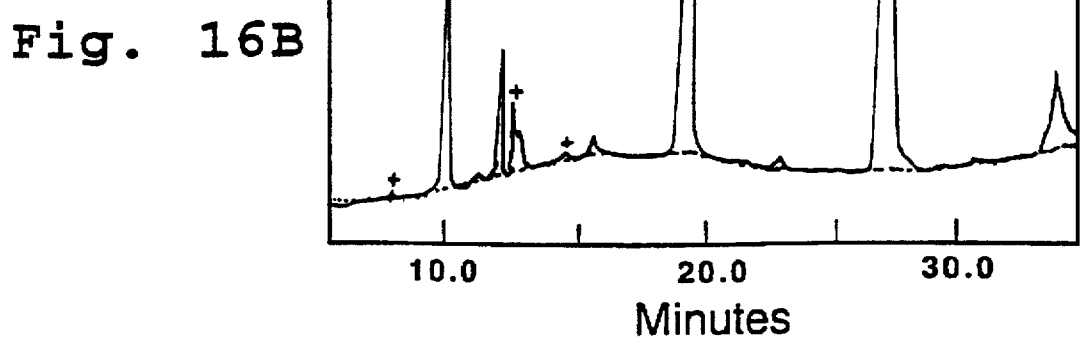
Figure 16C:
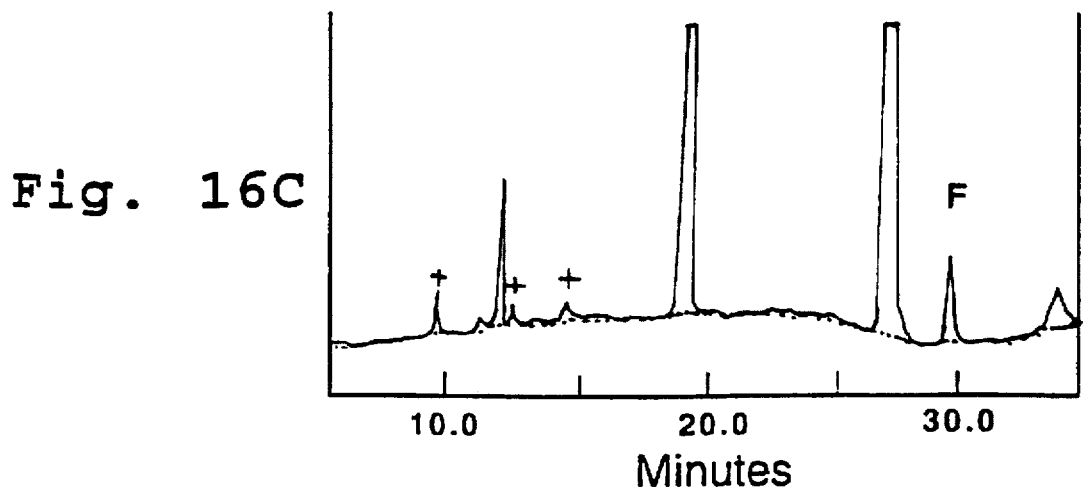
Figure 16D:
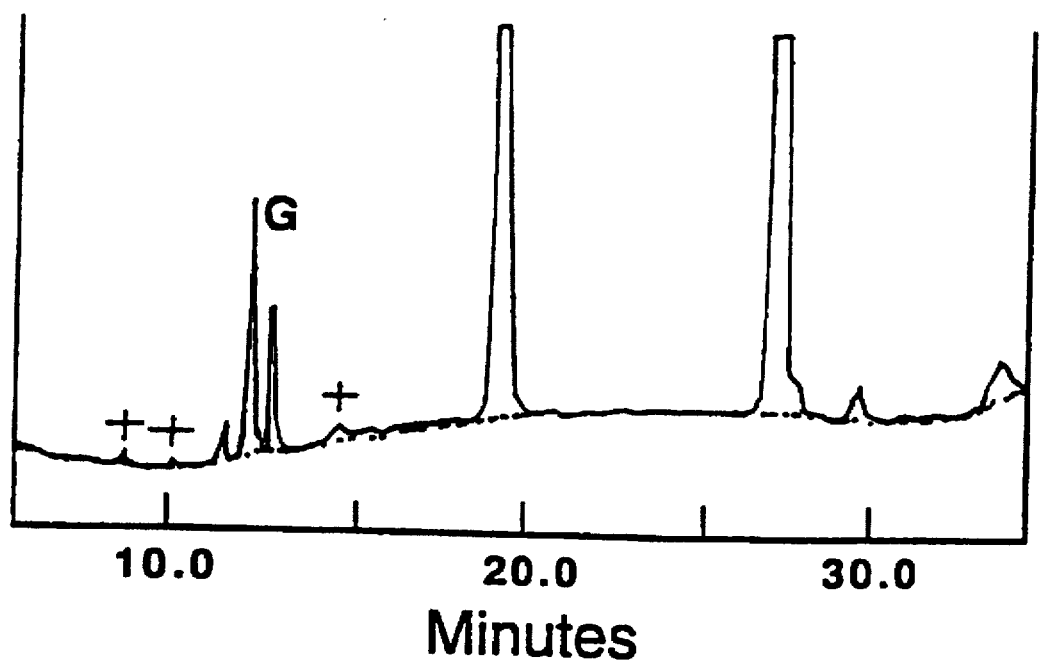
Figure 16E:
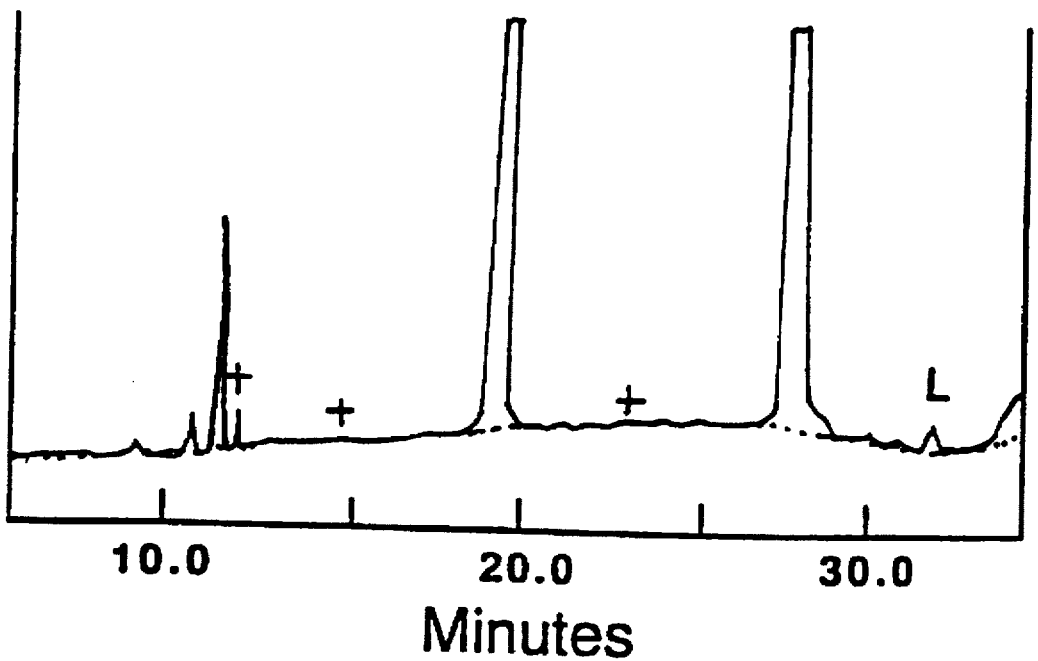

FIGS. 12A–12D and 13A–13C show C-terminal sequencing results for WRK-activated CPG beads (FIGS. 12A–12D) and DSS-activated CPG beads (FIGS. 13A–13D), where immobilization of the 11-mer was carried out in phosphate buffer at pH 6. As can be seen, the WRK-activated beads afforded thiohydantoin peaks of about the same magnitude as observed when the 11-mer had been immobilized in an organic solvent (FIGS. 10A–10D). In contrast, very little sequenceable material was observed with the DSS-activated beads where 11-mer had been immobilized in phosphate buffer (FIGS. 13A–13C). This last result suggests that a significant portion of the succinimide groups on the support were inactivated by water before being able to react with the 11-mer.

More generally, the results demonstrate the flexibility of the activated (enol ester) support of the invention in terms of the broad range of conditions under which sample immobilization can be achieved. The DSS-activated support permits sample immobilization in the presence of an organic solvent, but performs poorly under aqueous conditions. In contrast, the enol ester support allows sample loading under organic solvent conditions and aqueous conditions. This flexibility allows most polypeptide samples to be immobilized without requiring transfer to a special solvent. For example, where the polypeptide is provided in a buffered aqueous solution, the solution can be contacted directly with the support to effect immobilization. Moreover, the enol ester support avoids problems of sample solubility; that is, the support is compatible with the broad range of solvent conditions necessary to accomodate polypeptides having a variety of solubility characteristics.

The utility of the activated support of the invention for N-terminal sequencing of short peptides is illustrated by the study in Example 13A. In this study, a 12 residue peptide (SEQ ID NO:4) was spotted onto a WRK-activated PVDF membrane, and onto a standard PVDF membrane which was neither carboxylated nor otherwise derivatized. After drying, the membranes were placed in an automated sequencer and subjected to N-terminal Edman degradation (FIG. 17).

As can be seen from FIG. 17, the WRK-activated membrane allowed the peptide to be sequenced through the penultimate residue (hollow bars). In contrast, the non-activated membrane performed poorly, affording detectable peaks for only the first six or seven residues.

C.3 Binding Modes

According to another important aspect of the invention, it has been found that polypeptides which fail to bind covalently to the activated support may still be immobilized on the support by non-covalent interactions, particularly where activation was conducted using WRK. It is hypothesized that such non-covalent immobilization is based on favorable charge-charge interactions between support-bound sulfonate groups derived from the WRK reagent, and positively charged groups in the polypeptide (from ammonium, guanidinium, and/or imidazolium groups).

Figures 19, 20:
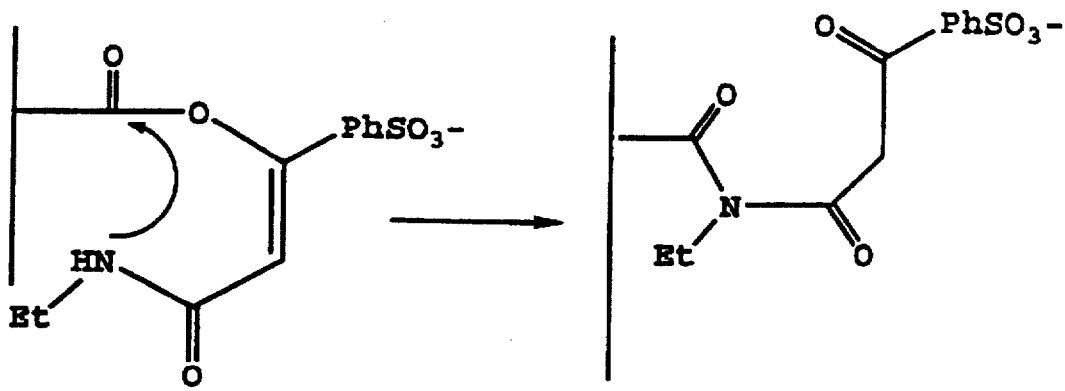
FIG. 19 shows an intramolecular rearrangement of a WRK-derived enol ester.
FIG. 20 shows the sequences of peptides used in illustrating the invention.

As can be seen from FIG. 3, the enol ester formed by WRK contains a sulfonate group attached to a phenyl ring. Thus, during the time the enol ester remains intact (i.e., does not react with polypeptide, base, or water), a sulfonate group is attached to the support at that enol ester site. In addition, permanently bound sulfonate groups can form on the support if the enol ester shown in FIG. 3 undergoes intramolecular acyl transfer, shown schematically in FIG. 19.

In one study, detailed in Example 11, apomyoglobin was immobilized on WRK-activated PVDF membranes under acidic (0.1% TFA, pH 2) or slightly basic (0.1M NaHCO$_3$, pH 8) conditions, and then rinsed with either 25% aqueous TFA ("acidic solution") or 50% diisopropylethylamine in methanol ("strongly basic solution"). Following additional wash steps, the membranes were subjected to amino acid analysis to determine the level of polypeptide still immobilized on the membrane (% recovery).

With reference to Table 2A (Example 11), the % recoveries (immobilization yields) were both about 50% when immobilization had been carried out at pH 8, regardless of which rinse solution was used. In contrast, immobilization carried out at pH 2 afforded significantly different recoveries, depending on the pH of the rinse step. When the membrane was rinsed with the acidic solution, the yield was very high (70%). However, when rinsing was done with the stronly basic DIEA solution, the % recovery dropped to about 5%.

A similar recovery pattern was observed when superoxide dismutase (SOD) was used as the polypeptide (Table 2B). Sample recoveries were about 50% in all cases except where sample loading was done at pH 2 and the rinse step at pH 8 (5.5% recovery).

These results indicate that when apomyoglobin is loaded at pH 8 (0.1M NaHCO$_3$), immobilization of the polypeptide is primarily by covalent attachment, since the % recovery is the same regardless of the rinse solution. When the sample is loaded at pH 2 (in 0.1% TFA), immobilization of the polypeptide is primarily by non-covalent binding to the membrane, as evidenced by the fact that the polypeptide can be washed from the support with the DIEA rinse solution. Presumably, this strongly basic rinse solution is able to disrupt favorable charge-charge interactions (salt bridges) by deprotonating positively charged groups on the polypeptide which interact with the sulfonate groups on the support.

In the study described in Example 12, the ability of non-covalently bound sample to remain associated with the support was tested under different denaturing conditions. The denaturing conditions included 2% "TRITON X-100", 1M urea, 1% sodium dodecylsulfate (SDS), and 10% "BRU-35". Water was included as a control.

As shown in Table 3 (Example 12), the percent recoveries of bound apomyoglobin were about 80% for all rinse conditions with the exception of 1% SDS. SDS differs from the other denaturants in that SDS is an anionic detergent, whereas urea, "TRITON X-100", and "BRU-35" are uncharged. The results are consistent with the results in Example 11, in that a negatively charged detergent can disrupt non-covalent immobilization, possibly by disrupting salt bridges, whereas neutral denaturants cannot.

More importantly, the results from Example 12 demonstrate that the activated support can bind polypeptides non-covalently despite the presence of denaturants added to solubilize the sample.

C.4 Combined N- and C-Terminal Sequencing

In another aspect, the activated support of the invention can be used for sequencing both N- and C-terminal amino acid residues in the same polypeptide sample. This capability makes the identification and/or characterization of a polypeptide sample much easier than previously possible because, as can be readily appreciated, having sequence information from both ends of the polypeptide can distinguish the polypeptide sample much more readily from other polypeptides than is possible when sequence information is available for only one end of the polypeptide. Moreover, where the polypeptide is one whose sequence has previously been determined, sequence analysis of a few residues at both ends of the polypeptide can provide rapid confirmation of the sample's identity.

Figure 18A:
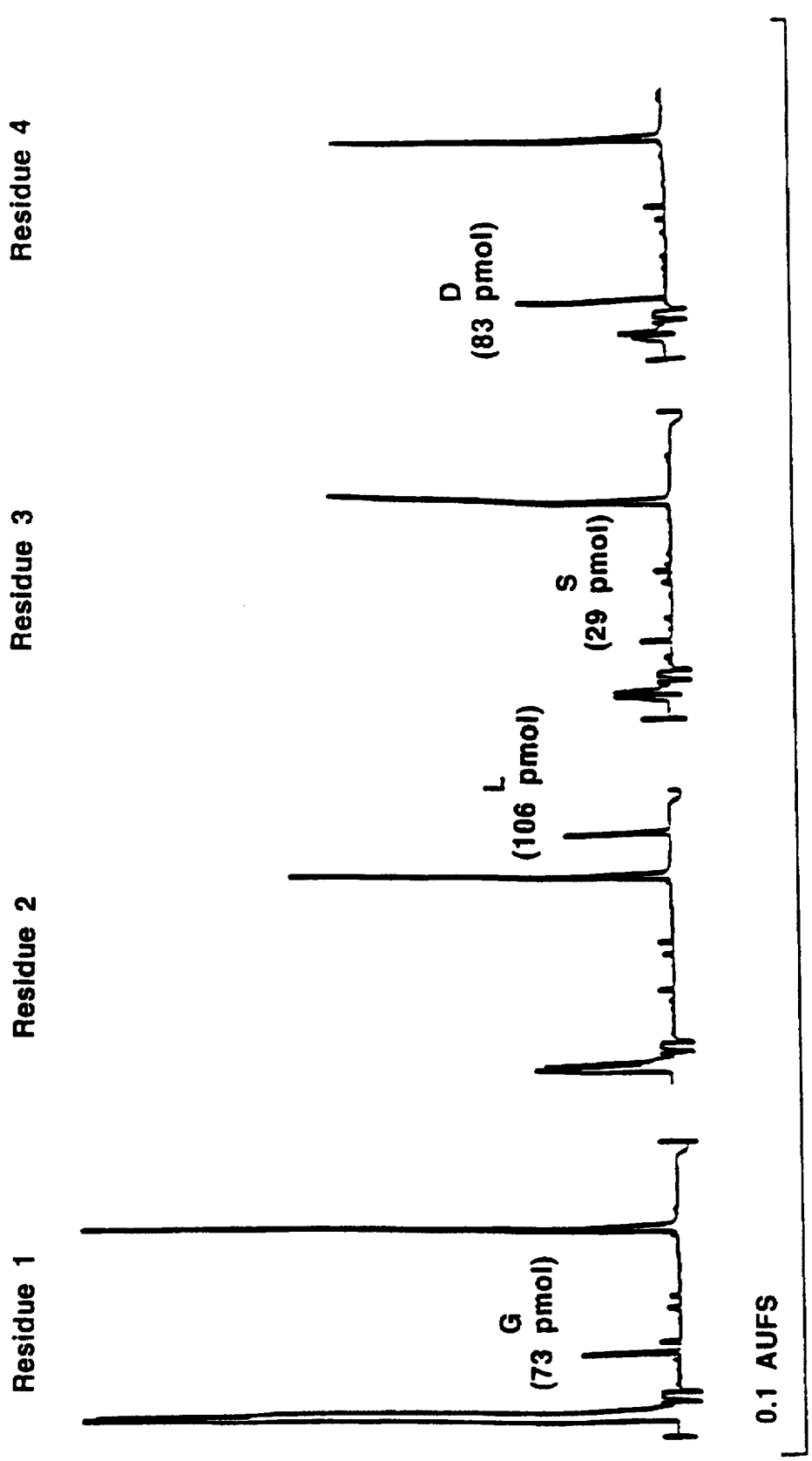
FIG. 18A shows HPLC chromatograms for first through fourth N-terminal sequencing cycles with apomyoglobin immobilized on a reactive support (PVDF membrane) of the invention.

Application of the method is illustrated in Example 13B. As detailed in the Example, apomyoglobin was immobilized on an WRK-activated PVDF membrane in 0.1% aqueous TFA. After air-drying, the membrane was placed in an automated sequencer and subjected to 5 cycles of N-terminal Edman degradation. HPLC chromatograms for the first four N-terminal residues are shown in FIG. 18A.

Figure 18B:
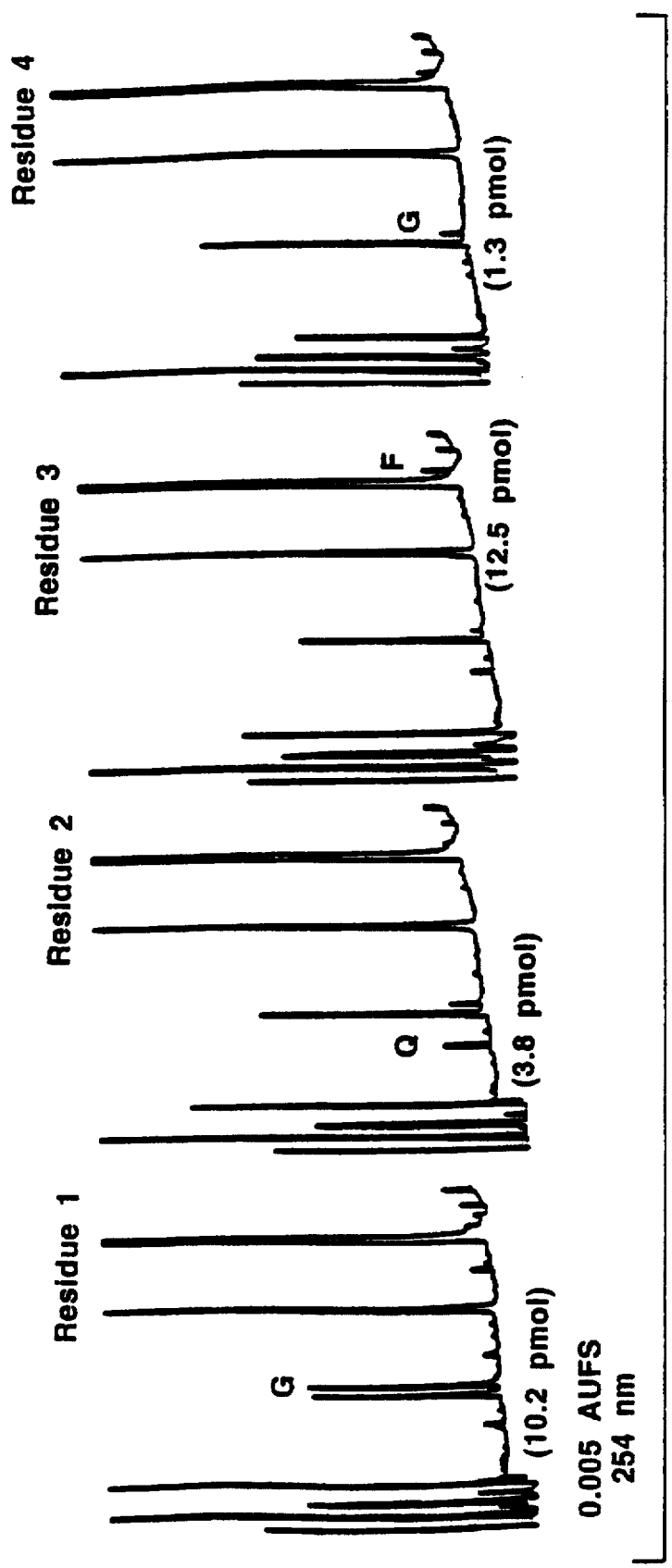
FIG. 18B shows HPLC chromatograms for first through fourth C-terminal sequencing cycles obtained using the same membrane and sample after the N-terminal sequencing shown in FIG. 18A.

After the fifth sequencing cycle, the same membrane was then subjected to four cycles of C-terminal sequence analysis. As shown in FIG. 18B, the first four C-terminal residues of the apomyoglobin sample were readily identified.

C.4 Long-term Stability of WRK-Activated Supports

In other experiments, the long-term stabilities of various WRK-activated supports were determined after storage in dry form for 3 to 6 months. In the study described below, the supports consisted of WRK-activated polystyrene resin prepared from aminomethyl polystyrene resin (see Examples 3 and 4; WRK-activated CPG beads (Examples 3 and 4); and WRK-activated PVDF membranes (Example 4). After WRK-activation of each support, the support was rinsed with acetone and allowed to air-dry. Each dry, activated support was then sealed in a scintillation vial or Eppendorf tube and stored at room temperature.

To assess polypeptide binding capacity, each support was incubated with a high concentration of polypeptide to maximize reaction of polypeptide with the support-bound enol ester groups that remained after storage. The supports were then subjected to C-terminal sequence analysis according to the procedures described in Example 14.

Sequence analysis of a twelve residue peptide (SEQ ID NO:2) immobilized on WRK-activated polystyrene resin is shown in FIGS. 14A–14D, where immobilization was carried out after the dried, activated support had been stored for three months. FIGS. 15A–15D show C-terminal sequence analysis of the same 12-mer, where immobilization had been carried out on activated CPG beads after storage of the dried, activated support for three months. FIGS. 16A–16E show C-terminal sequence analysis of apomyoglobin immobilized on a WRK-activated PVDF membrane which had previously been stored for six months in dried form.

With reference to FIGS. 14A–14D, 15A–15D, and 16A–6D, it can be seen that each activated support afforded strong alkylthiohydantoin signals through at least four C-terminal sequencing cycles after the dried, activated supports had been stored for several months. In addition, the magnitudes of the thiohydantoin peaks were comparable to those observed when immobilization was carried out using dried, activated supports that had been stored only a few days.

Thus, the present invention provides a ready-to-use activated solid support which can be stored for months under ambient conditions without significant reduction in its capacity to covalently bind polypeptides.

While the utility of the supports of the invention have been discussed with particular focus on amino acid sequencing, it can be appreciated that the support of the invention can also be used for coupling a polypeptide to a solid support for use in immunoassays; for example, where an antigen, antibody or $F_{ab}$ fragment are coupled to a support for binding and identifying a selected antibody or antigen in a sample.

It will be appreciated from the foregoing how various objects and features of the invention are met. The invention provides a dried, activated support and method useful for immobilizing polypeptides. The support shows long-term stability when stored in dried form and does not require any special storage conditions. Moreover, the support is compatible with aqueous conditions during sample loading and affords immobilization of polypeptides over a wide pH range. In particular, where the support comprises a PVDF membrane, the invention allows both N- and C-terminal sequence analysis of a polypeptide using a single membrane.

The following examples are offered to illustrate the invention and are not intended in any way to limit the scope thereof.

Materials

DITC glass beads were purchased from Sigma Chemical Co. (St. Louis, Mo.), and DITC-PVDF membranes ("SEQUELON") were from Millipore (Burlington, Mass.). Polyvinylidene difluoride membranes having surface-attached carboxylic acid groups ("carboxylated PVDF", or "PVDF-COOH") were obtained from Pall Corporation (Long Island, N.Y.). Aminopropyl controlled pore glass (CPG) beads and aminomethyl polystyrene beads were obtained from the Applied Biosystems Division of Perkin Elmer ("ABI", Foster City, Calif.).

N-terminal sequence analyses were performed on an ABI Model 476A Sequencer. C-terminal sequence analyses were performed on an ABI Model 477A Sequencer (Boyd et al., Anal Biochem., 206, 344–352, 1992). Amino acid composition analyses were performed using an ABI Model 421 Amino Acid Analyzer.

EXAMPLE 1

Preparation of Aminopropyl Glass Fiber Filter Paper

A circle of Whatman GF/F (11 cm. diameter) is first acid etched in neat triflouroacetic acid (TFA) for 1 hour at room temperature in a glass dish that is gently rocked. The etched paper is then placed on a Whatman #3 filter paper and air dried overnight.

The etched glass fiber filter paper is treated with (aminopropyl)triethoxysilane (2% in $H_2O$) in a plastic bag at room temperature for 3–5 hours. After washing several times with acetone the still damp aminopropyl-GF/F is cured in an oven at 100° for 45 minutes. The filter paper now has primary amine groups which can be quantified by ninhydrin assay. The amine content is typically 16 nmole/9 mm diameter disc.

EXAMPLE 2

Conversion of Amine Groups on Aminopropyl Glass Filter Paper into Carboxyl Groups Using Succinic Anhydride One gram of succinic anhydride, and 0.25 grams of dimethylaminopyridine (DMAP) were dissolved in 20 mL of acetonitrile. This solution was poured over a half-circle of aminopropyl glass fiber filter paper (Example 1) in a glass dish and allowed to react overnight at room temperature. After washing with acetonitrile several times, and a final rinse with acetone, the filter paper was allowed to air-dry. A small piece tested negative for amino groups by the ninhydrin assay.

EXAMPLE 3

Conversion of Amine Groups on Aminopropyl CPG Beads to Carboxyl Groups Using Succinic Anhydride 100 mg of aminopropyl CPG beads (45 umole $NH_2$/gram beads) were placed in a capped Eppendorf tube and shaken in about 1 mL of DMAP/succinic anhydride solution (Example 2) overnight at room temperature. The beads were washed several times with acetonitrile, acetone and then dried. The resultant material tested negative for amino groups by the ninhydrin assay.

EXAMPLE 4

Preparation of Activated Supports

A reactive ketenimine solution was generated in acetonitrile ($CH_3CN$) from N-ethyl-5-phenylisoxazolium sulfonate (Woodward's Reagent K, WRK) by mixing 0.063 g WRK (0.025 mole) and 0.5 mL diisopropylethylamine (DIEA, 0.025 mole) in 2 mL $CH_3CN$. The solution was used immediately upon complete dissolution of the solid WRK. A carboxylated support (e.g., carboxylated PVDF membrane or a carboxylated support from Example 2 or 3) was immersed in the solution for 4-6 hours, where the solution volume was adjusted to completely immerse the support. The resultant enol ester support was then washed several times with $CH_3CN$, lastly with acetone, and allowed to air-dry briefly. The activated supports were then kept in a capped Eppendorf or a sealed plastic bag.

EXAMPLE 5

Covalent Attachment of Apomyoglobin to Activated PVDF Membrane 120 nmoles of apomyoglobin was dissolved (incompletely) in 3 ml of 100 mM phosphate buffer, pH 7. The solution was sloshed over a sheet (286 mg) of activated-carboxyl-PVDF membrane (Example 4, prepared two days earlier) for 3 hours. Amino acid analysis indicated that 150 pmole protein/mg membrane were attached, an attachment efficiency of 35.8% (based on estimated amino group content of membrane prior to reaction with apomyoglobin). The yield of the first cycle of C-terminal sequence analysis (Example 14) was 35% (50 pmole "sequenceable" material out of the 150 pmoles protein attached to the membrane).

EXAMPLE 6

Covalent Attachment of Lysozyme to Activated PVDF Membrane

A solution of hen egg white lysozyme (1 mg/mL) in pH 7 phosphate buffer was sloshed over a sheet (283 mg) of activated-carboxyl-PVDF membrane as described in Example 5. Amino acid analysis indicated an attachment efficiency of 50%. Results of C-terminal sequence analysis (Example 14) are shown in FIGS. 6A-6D.

EXAMPLE 7

Attachment of Short Peptide to Activated PVDF Membrane

A fifteen residue peptide (2 mg, SEQ ID NO:1) was dissolved in 3 ml N-methyl pyrrolidone (NMP). The peptide solution was sloshed over a 286 mg sheet of activated carboxyl-PVDF membrane (activated and dried 2 days previously) for 3 hours. Unbound peptide was washed away using acetonitrile followed by acetone, and the sheet was then subjected to C-terminal sequence analysis (Example 14, FIGS. 7A-7D).

EXAMPLE 8

Use of Disuccinimidyl Suberate for Linking a Peptide to a Solid Support

Disuccinimidyl suberate (DSS, 15 mg) was dissolved in a mixture of N-methyl pyrrolidone (NMP, 720 µL), diisopropylethylamine (DIEA, 40 µL) and pyridine (40 µL). This mixture was added immediately upon complete dissolution to 100 mg of aminomethylpolystyrene beads (from ABI, 26 umole $NH_2$ group/g beads), and the reaction mixture was shaken at room temperature for 1-2 hours.

The resultant activated beads were washed twice with NMP. The peptide to be attached (typically about 10 umole) was dissolved in a mixture of 360 uL NMP and 40 uL pyridine. Upon complete dissolution, the peptide was added to the still wet activated beads and allowed to shake overnight at room temperature. The beads were washed several times the next day with NMP, water, and then acetonitrile, and dried by evacuated centrifugation. This procedure typically gave a loading of peptide of about 2 nmole peptide/mg sheet. The same procedure was also applied successfully to aminopropyl CPG beads.

EXAMPLE 9

Stability of Enol Ester Support

Three different WRK-activated supports were examined for retention of polypeptide-binding capacity after long-term storage in dried form. The dried supports used in the study were prepared by the general procedure described in Example 4, and after being allowed to air-dry, were stored in a scintillation vial or Eppendorf tube). No special storage conditions were used; in other words, there was no attempt to dessicate the activated supports or to store them under inert atmosphere or in a freezer.

The activated supports were tested by C-terminal sequence analysis for polypeptide-binding capacity after being stored for a few days, and again after storage for several months.

WRK-activated polystyrene resin (Example 4) was incubated for 3 hours with 3 mg of a twelve residue peptide (SEQ ID NO:2) in 0.5 ml dimethylformamide (DMF) and then C-terminal sequenced by the procedure described in Example 14. The results for the polystyrene resin after storage in dried form for three months are shown in FIGS. 14A-14D.

WRK-activated CPG beads were incubated in a similar fashion with the twelve residue peptide in DMF and sequenced as above. The results for the activated polystyrene resin after storage in dried form for three months are shown in FIGS. 15A–15D.

WRK-activated PVDF (Example 4) was incubated with 120 nmoles apomyoglobin as described in Example 5 and sequenced as above. The results for the activated membrane after storage in dried form for six months are shown in FIGS. 16A–16E.

EXAMPLE 10

Effect of pH on Binding of Sample to an Activated PVDF Membrane

Onto each of six 4-mm diameter activated PVDF membrane discs prepared as in Example 4 was spotted 4 µL of a solution containing 3 mg/mL apomyoglobin (500 pmole, from horse skeletal muscle) in one of the following: water, 0.1% aqueous TFA, pH 2, or 0.1M NaHCO$_3$, pH 5, 7, 8, or 9. The discs were allowed to air-dry for about 30 minutes at room temperature. Each disc was then washed twice with 0.5 mL water, twice with 0.5 mL 5% aqueous TFA, and once with 0.5 mL acetonitrile or methanol. Bound sample was quantitated by amino acid analysis (Materials and Methods), and the binding efficiency of the disc for each of the different buffer conditions was calculated as the ratio of bound sample to the amount of sample loaded (Table 1).

TABLE 1

| Loading Buffer | Bound[1] (pmole) | Recov. (%) |
|---|---|---|
| D.I. water | 277 | 55% |
| 0.1% TFA, pH 2 | 441 | 88% |
| 0.1M NaHCO3, pH 5 | 257 | 51% |
| 0.1M NaHCO3, pH 7 | 208 | 42% |
| 0.1M NaHCO3, pH 8 | 318 | 64% |
| 0.1M NaHCO3, pH 9 | 308 | 62% |

[1]Bound amount determined by amino acid analysis; 500 pmole apomyoglobin initially loaded.

EXAMPLE 11

Covalent Versus Non-Covalent Binding of Sample to an Activated PVDF Membrane Onto each of four 4-mm diameter activated PVDF membrane discs prepared as in Example 4 was spotted 5 µL of a solution containing 2.5 mg/mL apomyoglobin (750 pmole) in either 0.1% aqueous TFA, pH 2 (first pair of discs), or 0.1M NaHCO$_3$, pH 8 (second pair of discs). The discs were allowed to air-dry for about 30 minutes at room temperature. One disc from each pair was then washed two times with 500 µL of 25% aqueous TFA (acidic solution), followed by washes with 500 µL 5% aqueous acetonitrile and 500 µL neat acetonitrile. The other disc from each pair was washed with 500 µL 50% DIEA in methanol (basic solution), followed by washes with 500 µL 5% aqueous acetonitrile and 500 µL neat acetonitrile. The level of sample bound to each disc as a percentage of sample loaded is shown in Table 2A.

This procedure was also carried out using superoxide dismutase (200 pmole; from bovine erythrocytes) in place of apomyoglobin. The levels of sample retained on the membranes are shown in Table 2B.

TABLE 2

| Loading Buffer | Wash Solution | Yield (pmole) | recov. (%) |
|---|---|---|---|
| A. Apomyoglobin (750 pmole loaded) | | | |
| 0.1% TFA, pH 2 | Acidic | 524 | 70% |
| 0.1M NaHCO3, pH 8 | Acidic | 378 | 51% |
| 0.1% TFA, pH 2 | Basic | 36 | 4.8% |
| 0.1M NaHCO3, pH 8 | Basic | 356 | 48% |
| B. Superoxide Dismutase (200 pmole loaded) | | | |
| 0.1% TFA, pH 2 | Acidic | 102 | 51% |
| 0.1M NaHCO3, pH 8 | Acidic | 95 | 48% |
| 0.1% TFA, pH 2 | Basic | 11 | 5.5% |
| 0.1M NaHCO3, pH 8 | Basic | 96 | 48% |

EXAMPLE 12

Effect of Detergents On Sample Binding Strength of Activated PVDF Membrane

Onto each of five 4-mm diameter activated PVDF membrane discs prepared as in Example 4 was spotted 2.5 µL of a 1 mg/mL solution of apomyoglobin (150 pmole) in 0.1% aqueous TFA, pH 2. Each disc was then washed twice with 500 µL of one of the following solutions: water, 2% Triton X-100, 1M urea, 1% SDS, or 10% Brij-35. After the second wash, the support was washed twice with 500 µL water. Residual sample (calculated by amino acid analysis) bound to each disc as a percentage of the loaded amount is reported in Table 3.

TABLE 3

| Wash Reagent | Yield[1] (pmole) | recov. (%) |
|---|---|---|
| Water | 130 | 86% |
| 2% Triton X-100 | 121 | 81% |
| 1M Urea | 127 | 85% |
| 1% SDS | 21 | 14% |
| 10% Brij-35 | 112 | 75% |

[1]150 pmole apomyoglobin spotted on each membrane; loading buffer: 0.1% TFA, pH 2.

EXAMPLE 13

Sequence Analysis with Activated PVDF Membrane

A. N-Terminal Sequence Analysis of Peptide: Activated PVDF Membrane Versus Non-Activated, Non-Carboxylated PVDF Membrane Onto each of (i) a 4-mm diameter PVDF membrane (Problot Membrane from Applied Biosystems, Inc.; non-activated, non-carboxylated) and (ii) a 4-mm diameter of activated PVDF membrane disc prepared as in Example 4, was loaded 2 µL of a 12-residue peptide (SEQ ID NO:4; 7 µg/mL, 10 pmole total) dissolved in 0.1% aqueous TFA. After the disc had been allowed to air-dry, the disc was washed with 5% aqueous TFA (500 µL) and then acetonitrile (500 µL). The disc was then placed in an ABI Model 476A Sequencer and subjected to 12 cycles of Edman degradation. The identity and yield of the residue at each cycle are shown in FIG. 17.

B. Dual N- and C-Terminal Sequence Analysis Using a Single Sample Disc

Onto a 4-mm diameter activated PVDF membrane prepared as in Example 4 was loaded 2 µL of apomyoglobin (1 mg/mL, 120 pmole total) dissolved in 0.1% aqueous TFA. After the disc had been allowed to air-dry, the disc was placed in an ABI Model 476A Sequencer and subjected to 5 cycles of Edman degradation. HPLC chromatograms from the first four cycles of the analysis are shown in FIG. 18A. After the last cycle had been completed, the disc was removed from the Sequencer and transferred to an ABI Model 477A Sequencer. C-terminal sequence analysis was then carried out as described in Example 14. The results are shown in FIG. 18B.

EXAMPLE 14

Sequence Analysis of Immobilized Peptides

Proteins and peptides attached to a solid support as described above were converted to C-terminal thiohydantoins as described below and then sequenced from the C-terminus using an Applied Biosystems Model 477A Protein Sequencer. A 10% solution of DIEA (diisopropylethylamine) in acetonitrile was loaded in the S1 position of the Model 477A, and an 8% solution of diphenylchlorophosphate in acetonitrile was placed in the X1 position.

The following reaction steps were carried out at 55° C. After the protein- or peptide-derivatized support had been loaded in the sequencer, equivolume aliquots of the DIEA and diphenylchlorophosphate solutions were delivered to the membrane in an amount sufficient to completely wet the membrane. After a 5 minute pause, delivery of the DIEA and diphenylchlorophosphate solutions to the membrane was repeated once. The membrane was then washed with acetonitrile to remove residual chlorophosphate compound. After another 5 minute pause, an aliquot of 1% ammonium thiocyanate in acetonitrile was delivered to the membrane, followed by exposure of the membrane to trifluoroacetic acid (TFA) vapor for 60 seconds. After a 5 minute pause, delivery of 1% ammonium thiocyanate and TFA vapor was repeated 1–5 additional times, with intervening 5 minute pauses. Residual reagents were then washed from the membrane using acetonitrile.

If esterification of the carboxylate groups of aspartate and glutamate side chains was desired, an esterification step was included after formation of peptidyl-thiohydantoin and washing of the membrane with acetonitrile as above. In the esterification step, the membrane was washed briefly (e.g., 1 minute) with methanol, followed by treatment with TFA vapor for 60 seconds. After a 5 minute pause, the membrane was washed with acetonitrile.

Sequencing was performed essentially as described in U.S. Pat. No. 5,185,266. In this procedure, the C-terminal thiohydantoin is reacted with an alkylating reagent to make the thiohydantoin a better leaving group. TMS-ITC or ammonium thiocyanate and TFA vapor are then used to cleave the thiohydantoin adduct from the remaining peptide to form a thiohydantoin of the next-in amino acid residue. Cleaved thiohydantoin adducts were isolated and identified by the methods presented in U.S. Pat. No. 5,185,266.

EXAMPLE 15

A. Spotting Sample on Membrane Support

On a 4 mm diameter disc of WRK-activated carboxylated PVDF membrane was spotted 5 μL of lysozyme (1 mg/mL) in pH 7 phosphate buffer, in two 2.5μ aliquots. The disc was allowed to air-dry and then placed in an automated sequencer for N- or C-terminal sequence analysis.

B. Spin-Filtration

For immobilization of polypeptides by centrifugation (spin filtration), a centrifuge tube insert device was constructed by modifying a "PROSPIN" insert device (ABI, Part No. 401,256) to contain a 4 mm diameter WRK-activated PVDF (8000 MW cutoff). The insert was then placed in a 1.5 mL Eppendorf tube, and polypeptide sample solution (50–100 μL) typically containing 500 pmole of protein was added. The tube/insert assembly was then placed in a microfuge and centrifuged at 8000 rpm for about 1 hour. After air-drying, the support could be used for sequence analysis. Typically, 50–60% of the protein sample was immobilized on the membrane, as determined by amino acid analysis.

Although the present invention has been described and illustrated with respect to particular solid supports and polypeptides, it will be appreciated that a variety of modifications and changes may be made without departing from the invention.

---

It is claimed:

1. A method for immobilizing a polypeptide on a solid support, comprising providing an essentially dry polyvinylidene difluoride membrane having an enol ester group and a sulfonate group covalently attached thereto, wherein the enol ester group and sulfonate group are formed by reacting a polyvinylidene diflouride membrane that has bound carboxylic acid groups with 2-ethyl-5'-phenylisoxazolium sulfonate, and contacting a polypeptide with the membrane under conditions effective to bind the polypeptide to the membrane covalently or non-covalently.

2. The method of claim 1, wherein said polypeptide contains a primary amino group, and said conditions are effective to bind the polypeptide covalently to the membrane by reaction of the primary amino group with said enol ester group.

3. The method of claim 1, wherein the polypeptide is dissolved in an aqueous solution when contacting said membrane.

4. The method of claim 1, wherein the polypeptide is dissolved in an organic solvent when contacting said membrane.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: synthetic 15 residue peptide ( x i ) SEQUENCE DESCRIPTION: SEQ ID NO:1:

```
         Ala Lys Gly Lys Gly Lys Leu Tyr Phe Gly Leu Tyr Gln Phe Gly
          1           5                   10                      15
```

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (C) INDIVIDUAL ISOLATE: synthetic 12 residue peptide (xi) SEQUENCE DESCRIPTION: SEQ ID NO:2:

```
         Gly Ala Pro Lys Gly Lys Gly Lys Tyr Phe Leu Tyr
          1           5                   10
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (C) INDIVIDUAL ISOLATE: synthetic 11 residue peptide (xi) SEQUENCE DESCRIPTION: SEQ ID NO:3:

```
         Lys Gly Lys Gly Lys Gly Leu Gln Asn Leu Ala
          1           5                   10
```

(2) INFORMATION FOR SEQ ID NO:4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (C) INDIVIDUAL ISOLATE: synthetic 12 residue peptide (xi) SEQUENCE DESCRIPTION: SEQ ID NO:4:

```
         Leu Glu His Phe Arg Lys Gly Ile Gln Val Asn Tyr
          1           5                   10
```